(12) United States Patent
Kuroda et al.

(10) Patent No.: US 12,233,150 B2
(45) Date of Patent: Feb. 25, 2025

(54) ORAL CARE COMPOSITIONS COMPRISING STAR-SHAPED POLYMERS

(71) Applicants: THE REGENTS OF THE UNIVERSITY OF MICHIGAN, Ann Arbor, MI (US); COLGATE-PALMOLIVE COMPANY, Piscataway, NJ (US)

(72) Inventors: Kenichi Kuroda, Ann Arbor, MI (US); Carl P. Myers, Piscataway, NJ (US); Guillaume A. Picquet, Piscataway, NJ (US); Lynette A. Zaidel, Piscataway, NJ (US)

(73) Assignees: REGENTS OF THE UNIVERSITY OF MICHIGAN, Ann Arbor, MI (US); COLGATE-PALMOLIVE COMPANY, Piscataway, NJ (US)

( * ) Notice: Subject to any disclaimer, the term of this patent is extended or adjusted under 35 U.S.C. 154(b) by 758 days.

(21) Appl. No.: 17/621,778

(22) PCT Filed: May 28, 2020

(86) PCT No.: PCT/US2020/034826
§ 371 (c)(1),
(2) Date: Dec. 22, 2021

(87) PCT Pub. No.: WO2020/243237
PCT Pub. Date: Dec. 3, 2020

(65) Prior Publication Data
US 2023/0000755 A1  Jan. 5, 2023

Related U.S. Application Data

(60) Provisional application No. 62/854,869, filed on May 30, 2019.

(51) Int. Cl.
*A61K 8/81* (2006.01)
*A61Q 11/00* (2006.01)

(52) U.S. Cl.
CPC ............ *A61K 8/8152* (2013.01); *A61Q 11/00* (2013.01); *A61K 2800/544* (2013.01)

(58) Field of Classification Search
CPC .. A61K 8/8152; A61Q 11/00; C08F 220/1804
See application file for complete search history.

(56) References Cited

U.S. PATENT DOCUMENTS

| | | | |
|---|---|---|---|
| 3,535,421 A | 10/1970 | Briner et al. | |
| 3,678,154 A | 7/1972 | Widder et al. | |
| 4,885,155 A | 12/1989 | Parran, Jr. et al. | |
| 7,939,306 B2 | 5/2011 | Szeles et al. | |
| 2010/0233595 A1* | 9/2010 | Takahashi | C08F 2/38 |
| | | | 430/7 |

FOREIGN PATENT DOCUMENTS

WO  WO-84/04546 A1  11/1984

OTHER PUBLICATIONS

International Application No. PCT/US2020/034826, International Search Report and Written Opinion, mailed Oct. 9, 2020.
Balls et al., The milk-clotting action of papain, J. Biol. Chem., 121:737-45 (1937).
Mortazavian et al., Understanding the Role of Shape and Composition of Star-Shaped Polymers and their Ability to Both Bind and Prevent Bacteria Attachment on Oral Relevant Surfaces, J. Funct. Biomater., 10(4):56 (2019).
Luo et al., Synthesis of Heteroarm Star-Shaped Polymer by The Use of Polyfunctional Chain-Transfer Agent Via Conventional Free Radical Polymerization, Chinese Journal of Polymer Science, 26(3):321-9 (2008).
Zhang et al., Preventing plaque formation with carboxyl substituent polymers, Toothpaste Industry, pp. 23-29 (1994).

(Continued)

*Primary Examiner* — Andrew S Rosenthal
(74) *Attorney, Agent, or Firm* — MARSHALL, GERSTEIN & BORUN LLP

(57) ABSTRACT

Provided herein are star-shaped polymers and methods of use thereof. Also provided are oral compositions comprising a star-shaped polymer and an orally acceptable carrier and methods of using same. The star-shaped polymers, as provided herein, have a structure according to Formula (I).

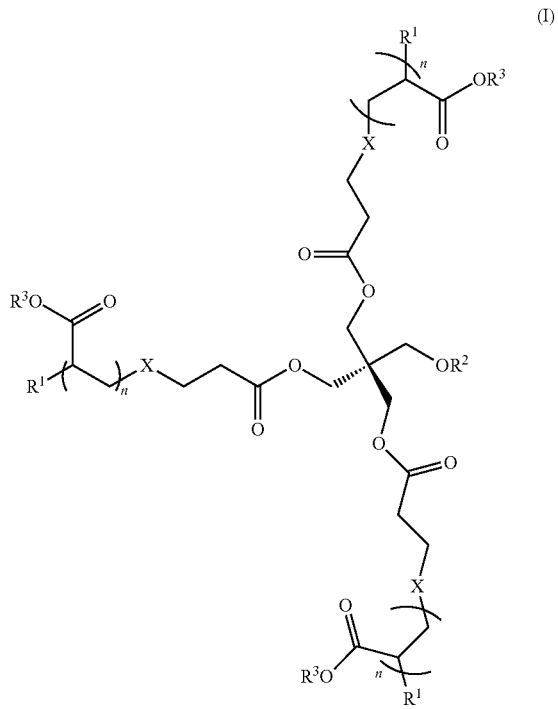

21 Claims, 3 Drawing Sheets

(56) References Cited

OTHER PUBLICATIONS

Kong et al., Synthesis of amphiphilic heteroarm star-shaped polymer by the use of polyfunctional chain-transfer agent via contentional free radical polymerization, Acta Polymerica Sinica, pp. 102-106 (2008).
Chinese Patent Application No. 202080040499, Office Action, dated Feb. 18, 2024.

* cited by examiner

ORAL CARE COMPOSITIONS COMPRISING STAR-SHAPED POLYMERS

CROSS REFERENCE TO RELATED APPLICATIONS

This application is the U.S. national phase of PCT Application No. PCT/US20/34826, filed on May 28, 2020, which claims the benefit of U.S. Provisional Application No. 62/854,869, filed May 30, 2019, the entire disclosures of which are hereby incorporated by reference in their entirety.

FIELD OF THE INVENTION

The disclosure relates generally to an oral care composition comprising a star-shaped polymer, and methods of using same. More particularly, the disclosure relates to an oral care composition comprising a star-shaped polymer and an orally acceptable carrier for use in inhibiting bacterial attachment to teeth.

BACKGROUND

Oral hygiene is one of the most important aspects of personal care among consumers. Consumers all over the world use different types of products for oral care as a part of maintaining dental hygiene. People routinely brush their teeth with a toothbrush and a dentifrice which includes toothpaste or toothpowder or mouthwash at least two times a day. Use of such brushing ensures maintaining good oral hygiene by minimizing oral bacteria that accumulate in the mouth over the course of sleeping in the night or during the course of the day when people eat their food and consume beverages. Brushing regularly thus minimizes problems like cavities, tartar, gingivitis, caries, and bad breath, also known as halitosis.

In spite of brushing teeth twice a day, many people suffer from various forms of one or more of the above named diseases associated with dental hygiene and this is believed to be caused, in part, by the formation of oral biofilms, or dental plaque, on tooth surfaces.

A tooth is comprised of an inner dentin layer and an outer hard enamel layer that is the protective layer of the tooth. The enamel layer is composed of hydroxyapatite (HAP) mineral crystals that create a somewhat porous surface. Dental plaque occurs in the form of a film, on virtually all dental surfaces, such as the HAP-containing enamel layer. Dental plaque is a byproduct of microbial growth, and comprises a dense microbial layer consisting of a mass of microorganisms embedded in a polysaccharide matrix. Plaque itself adheres firmly to dental surfaces, for example, tooth enamel, and is removed only with difficulty even through a rigorous brushing regimen. Moreover, plaque rapidly reforms on the tooth surface after it is removed. Plaque may form on any part of the tooth surface, and is found particularly at the gingival margin, in cracks in the enamel, and on the surface of dental calculus. The danger associated with the formation of plaque on the teeth lies in the tendency of plaque to build up and eventually produce gingivitis, periodontitis and other types of periodontal disease, as well as dental caries and dental calculus.

SUMMARY

Provided herein are oral care compositions comprising a star-shaped polymer and an orally acceptable carrier, wherein the star-shaped polymer has a structure according to Formula (I):

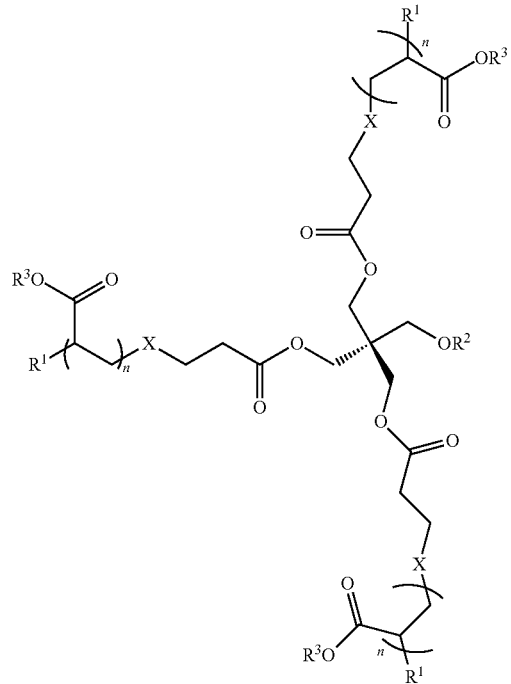

wherein each $R^1$ independently comprises H or an acrylate polymer, each n independently is 5 to 500, for example, 10 to 400, or 15 to 300, each X is independently O, $NR^4$, or S, wherein $R^4$ comprises H or $C_{1-6}$alkyl, $R^2$ comprises H, $C_{1-8}$alkyl, or a functionalized acrylate polymer, and each $R^3$ independently comprises H, $C_{1-8}$alkyl, or $C_{1-8}$alkyl phosphate.

The disclosure further provides methods of inhibiting bacterial attachment to teeth comprising administering to the subject an oral care composition comprising a star-shaped polymer having the structure according to Formula (I) and an orally acceptable carrier.

Also provided is a star-shaped polymer having a structure according to Formula (I).

Further provided are methods of forming a layer on a tooth surface comprising administering to the subject an oral care composition comprising a star-shaped polymer having the structure according to Formula (I) and an orally acceptable carrier.

Further aspects and advantages will be apparent to those of ordinary skill in the art from a review of the following detailed description. While the compositions and methods are susceptible of embodiments in various forms, the description hereafter includes specific embodiments with the understanding that the disclosure is illustrative, and is not intended to limit the disclosure to the specific embodiments described herein.

DETAILED DESCRIPTION

Figure 1:
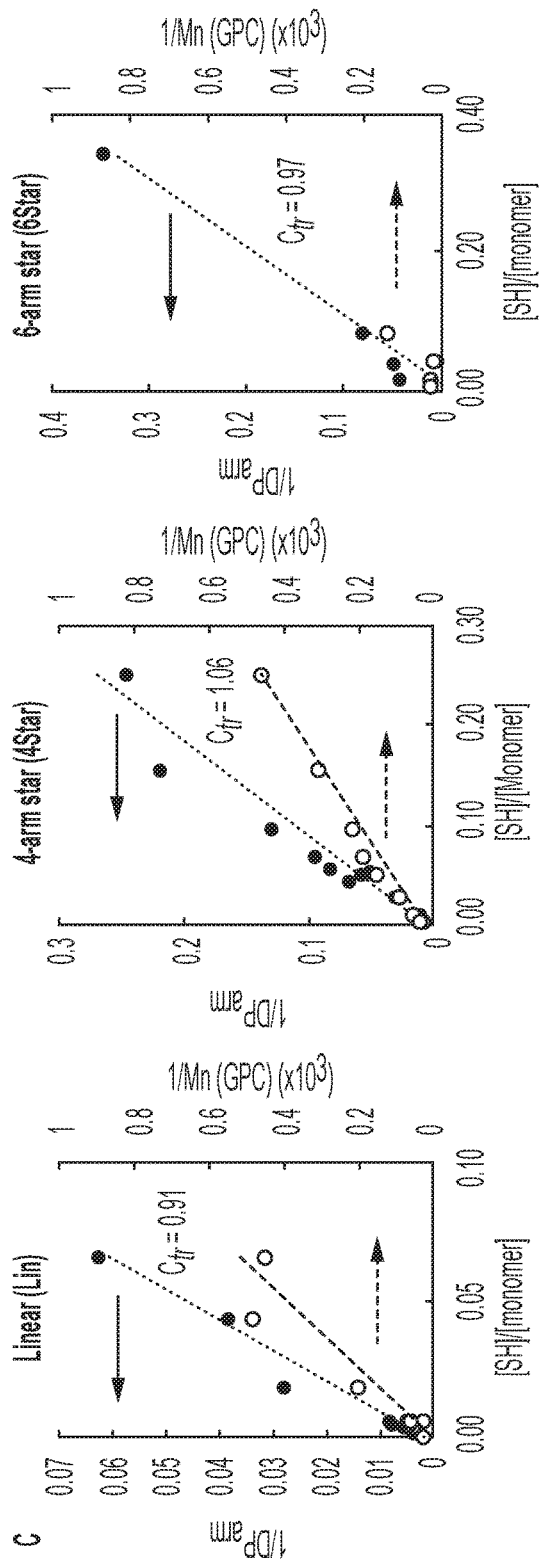
FIG. 1 shows Mayo plots demonstrating the polymerization and synthesis of star-shaped polymers via a chain transfer process.

The disclosure provides a star shaped polymer. The disclosure also provides an oral care composition comprising a star-shaped polymer and an orally acceptable carrier, wherein the star-shaped polymer has a structure according to Formula (I):

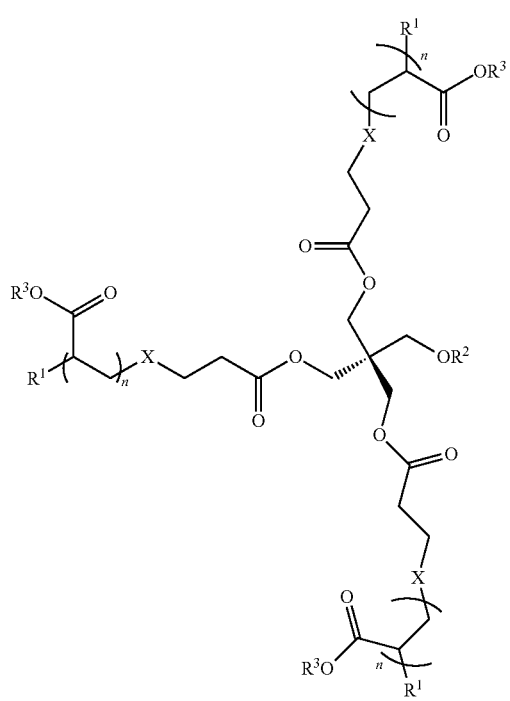

wherein the substituents are described in detail, below.

The star-shaped polymers described herein can be used in oral care compositions to inhibit the attachment and growth of microbial films on tooth surfaces. For example, when the polymers are used in oral care compositions, they bind to hydroxyapatite (HAP) surfaces, thereby facilitating repelling and/or preventing bacterial attachment to tooth surfaces, making the utilization of these polymers in oral care compositions particularly advantageous.

Star-Shaped Polymers

Provided herein are star-shaped polymers. Also provided are oral care compositions comprising a star-shaped polymer and an orally acceptable carrier. The star-shaped polymer has a structure according to Formula (I):

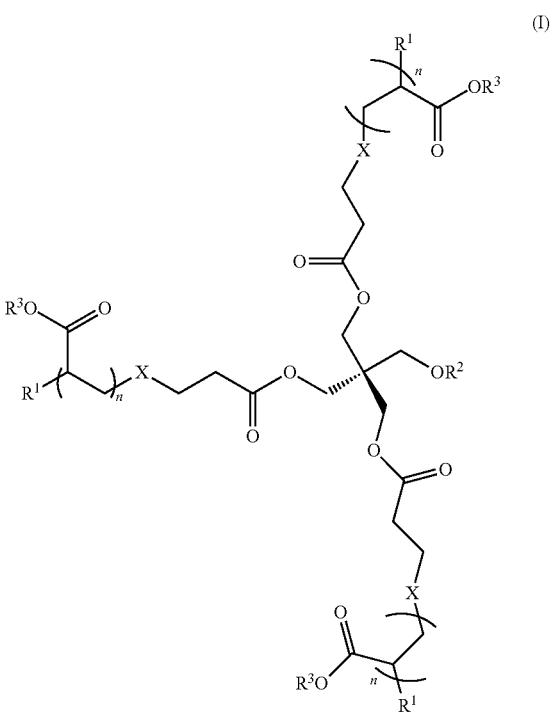

wherein,
each $R^1$ independently comprises H or an acrylate polymer;
each n independently is 5 to 500, for example, 10 to 400, or 15 to 300
each X is independently O, $NR^4$ or S, wherein $R^4$ comprises H or $C_{1-6}$alkyl;
$R^2$ comprises H, $C_{1-8}$alkyl, or a functionalized acrylate polymer; and,
each $R^3$ independently comprises H, $C_{1-8}$alkyl, or $C_{1-8}$alkyl phosphate.

As provided herein, each $R^1$ independently comprises H or an acrylate polymer. The various $R^1$ moieties may be the same or different throughout the star-shaped polymer. In some embodiments, each $R^1$ comprises H. In other embodiments, each $R^1$ comprises an acrylate polymer.

As used herein, an "acrylate polymer" refers to any polymer formed from the polymerization of a reaction mixture including acrylate monomers. Accordingly, an "acrylate polymer" can refer to a homopolymer formed from the polymerization of a single type of acrylate monomer (e.g. polyacrylic acid), or a copolymer formed from the polymerization of two or more types of monomers, wherein at least one type of monomer is an acrylate monomer. The acrylate polymer can be a linear homopolymer, a linear copolymer, a branched homopolymer, or a branched copolymer. Suitable acrylate monomers that can be used in preparation of the acrylate polymer can include, for example, acrylic acid or its derivatives, methacrylic acid or its derivatives, and combinations of the foregoing. Acrylic acid derivatives include, but are not limited to, methyl acrylate, ethyl acrylate, butyl acrylate, sec-butyl acrylate, tert-butyl acrylate, and 2-ethylhexyl acrylate. Methacrylic acid derivatives include, but are not limited to methyl methacrylate, ethyl methacrylate, butyl methacrylate, sec-butyl methacrylate, tert-butyl methacrylate, and 2-ethylhexyl methacrylate. Additional suitable acrylic acid derivatives include phosphates of acrylic acid or its derivatives and phosphates of methacrylic acid and its derivatives including but not limited to ethylene methacrylate phosphate (also known as 2-hydroxyethyl methacrylate phosphate) and other alkyl acrylate phosphates and alkyl methacrylate phosphates. Other monomers suitable for use in an acrylate copolymer include, but are not limited to, other phosphate-bearing monomers, phosphonate-bearing monomers, acrylamide, methacrylamide, and styrene monomers. In embodiments, the $R^1$ comprises a linear acrylate polymer. In embodiments, $R^1$ comprises a branched acrylate polymer. In embodiments, the acrylate polymer is selected from the group consisting of polymethacrylate, poly(ethyl acrylate), poly(propyl acrylate), poly(butyl acrylate), and poly($C_{1-8}$alkyl phosphate acrylate). In some embodiments, $R^1$ comprises an acrylate copolymer, wherein said copolymer is prepared from the polymerization of a reaction mixture comprising methacrylate in combination with any one or more monomers, as provided above. For example, in some cases, the mole percentage of methacrylate in the star-shaped polymer of the oral care composition according to the disclosure ranges from about 5 to about 70 mol. %, from about 25 to about 65 mol. %, or about 40 to about 60 mol. %, for example, about 5, 10, 15, 20, 25, 30, 34, 35, 40, 45, 50, 56, 57, 60, 65 or 70 mol. %. The mole percentage of methacrylate, or any other monomer used in the preparation of the star-shaped polymer, can be determined by analysis of the $^1$H NMR spectra of the polymers.

In embodiments, $R^1$ can be selected in view of the other formula parameters such that the star-shaped polymer, as a whole, remains substantially soluble in water. The ability of the polymer to bind to HAP, thereby repelling or preventing bacterial attachment while maintaining water-solubility is particularly advantageous for use in oral care compositions, as provided herein, as it allows for ease in formulation of the composition, as well as in application of the composition to an oral cavity of a human or mammalian subject.

As provided herein, each $R^3$ independently comprises H, $C_{1-8}$alkyl, or $C_{1-8}$alkyl phosphate. In some embodiments, $R^3$ comprises H. In some embodiments, $R^3$ comprises $C_{1-8}$alkyl. In some embodiments, $R^3$ comprises $C_{1-8}$alkyl phosphate. The various $R^3$ moieties may be the same or different in a given segment of the star-shaped polymer and also more generally throughout the star-shaped polymer. As used herein, the term "alkyl" refers to straight chained and branched saturated and hydrocarbon groups containing one to thirty carbon atoms, for example one to twenty carbon atoms, or one to ten carbon atoms. The term $C_n$ means the alkyl group has "n" carbon atoms. For example, $C_4$alkyl refers to an alkyl group that has 4 carbon atoms. $C_{1-8}$alkyl refers to an alkyl group having a number of carbon atoms encompassing the entire range (i.e., 1 to 8 carbon atoms), as well as all subgroups (e.g., 1-7, 2-7, 1-6, 2-6, 1-5, 2-5, 3-5, 3-6, 4-8, 4-7, 5-8, 1, 2, 3, 4, 5, 6, 7, and 8 carbon atoms). Nonlimiting examples of alkyl groups include, but are not limited to, methyl, ethyl, n-propyl, isopropyl, n-butyl, sec-butyl (2-methylpropyl), t-butyl (1,1-dimethylethyl), n-pentyl, 2-methylbutyl, 3-methylbutyl, 2,2-dimethylpropyl, n-hexyl, 2-methylpentyl, 3-methylpentyl, 4-methylpentyl, 2,2-dimethylbutyl, 2,3-dimethylbutyl, 3,3-dimethylbutyl, 2-ethylbutyl, n-heptyl, 2-methylhexyl, 3-methylhexyl, 2,2-dimethylpentyl, 2,3-dimethylpentyl, 2,4-dimethylpentyl, 3,3-dimethylpentyl, n-octyl, 2-methylheptyl, 3-methylheptyl, 4-methylheptyl, 2,2-dimethylheptyl, 2-ethylhexyl, 3-ethylhexyl, 3,4-dimethylhexyl, 3,4-diethylbutyl, or 2-methyl-3-ethylpentyl. Unless otherwise indicated, an alkyl can be a substituted alkyl or an unsubstituted alkyl. In some cases, each $R^3$ is methyl. In some cases, each $R^3$ is t-butyl. In some embodiments, each $R^3$ is $C_{1-8}$alkyl phosphate. As used herein, the term "alkyl phosphate" refers to a phosphate group in which one or more of the O atoms of the phosphate is substituted with an alkyl group. Nonlimiting examples of alkyl phosphate groups include, but are not limited to, monomethyl phosphate, dimethyl phosphate, trimethyl phosphate, hexyl phosphate, or diethylhexyl phosphate.

As provided herein, each X is independently O, $NR^4$, or S, wherein $R^4$ comprises H or $C_{1-6}$alkyl. In some embodiments, X is O. In some cases, X is NH. In some cases, X is $NC_{1-6}$ alkyl. For example, X can be N, wherein N is substituted with methyl, ethyl, n-propyl, isopropyl, n-butyl, sec-butyl (2-methylpropyl), t-butyl (1,1-dimethylethyl), n-pentyl, 2-methylbutyl, 3-methylbutyl, 2,2-dimethylpropyl, n-hexyl, 2-methylpentyl, 3-methylpentyl, 4-methylpentyl, 2,2-dimethylbutyl, 2,3-dimethylbutyl, 3,3-dimethylbutyl, or 2-ethylbutyl. In some cases, X is S. The various X moieties may be the same or different in a given segment of the star-shaped polymer and also more generally throughout the star-shaped polymer.

As provided herein, $R^2$ comprises H, $C_{1-8}$alkyl, or a functionalized acrylate polymer. In some embodiments, $R^2$ comprises H. In some embodiments, $R^2$ comprises $C_{1-8}$alkyl. In some embodiments, $R^2$ comprises a functionalized acrylate polymer. As used herein, "functionalized acrylate polymer" is similar to "acrylate polymer" as described above, but further includes a moiety that can facilitate chain transfer and chain extension. For example, an acrylate polymer (e.g. an acrylate homopolymer or acrylate copolymer, as described above) further comprising a thiol or amino group can provide a functionalized acrylate polymer in the star-shaped polymer. In various cases, $R^2$ comprises a functionalized acrylate homopolymer. In some cases, $R^2$ comprises a functionalized acrylate copolymer. For example, in some cases, $R^2$ comprises a functionalized acrylate copolymer having a

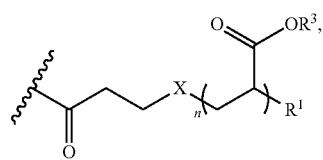
(IA)
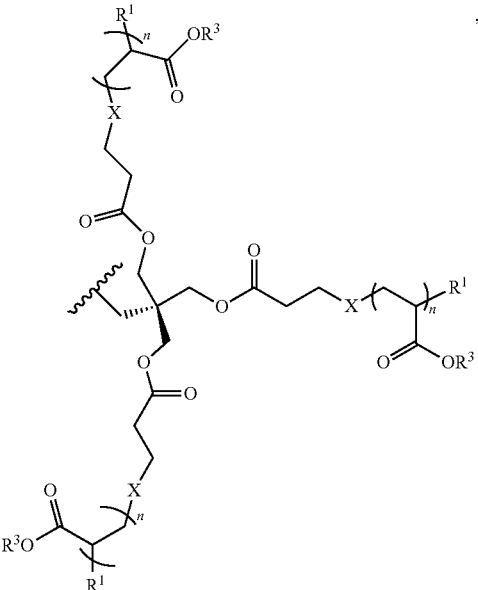
(IB)
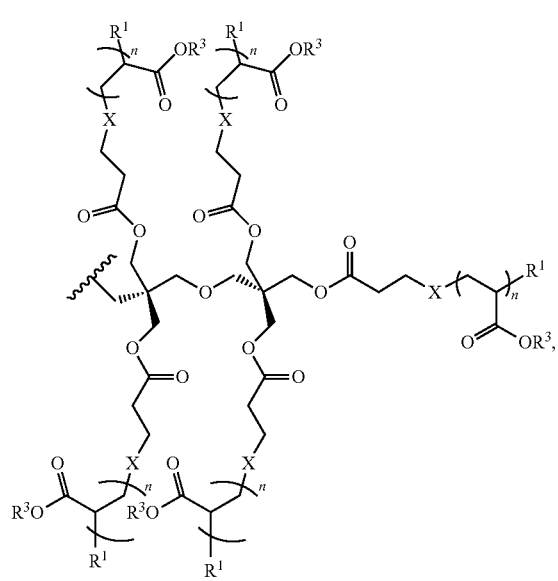
(IC)

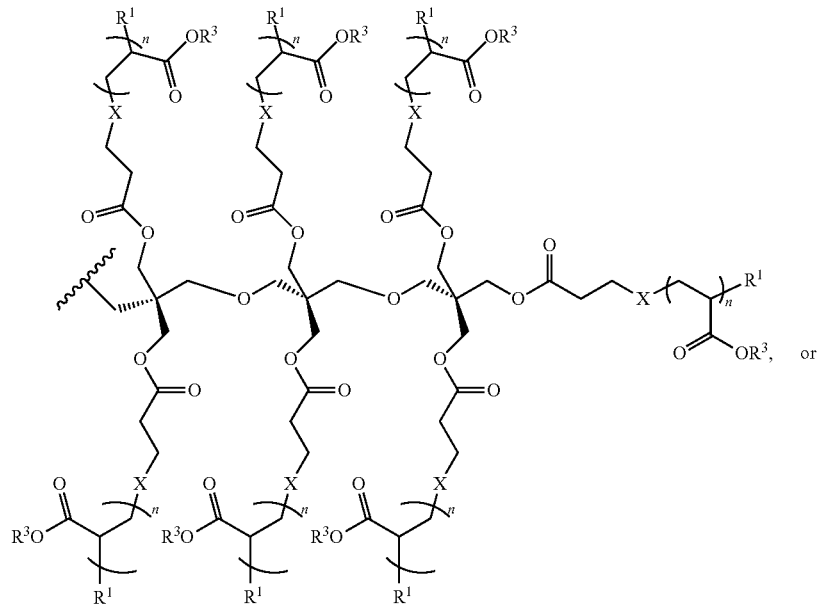

(ID)

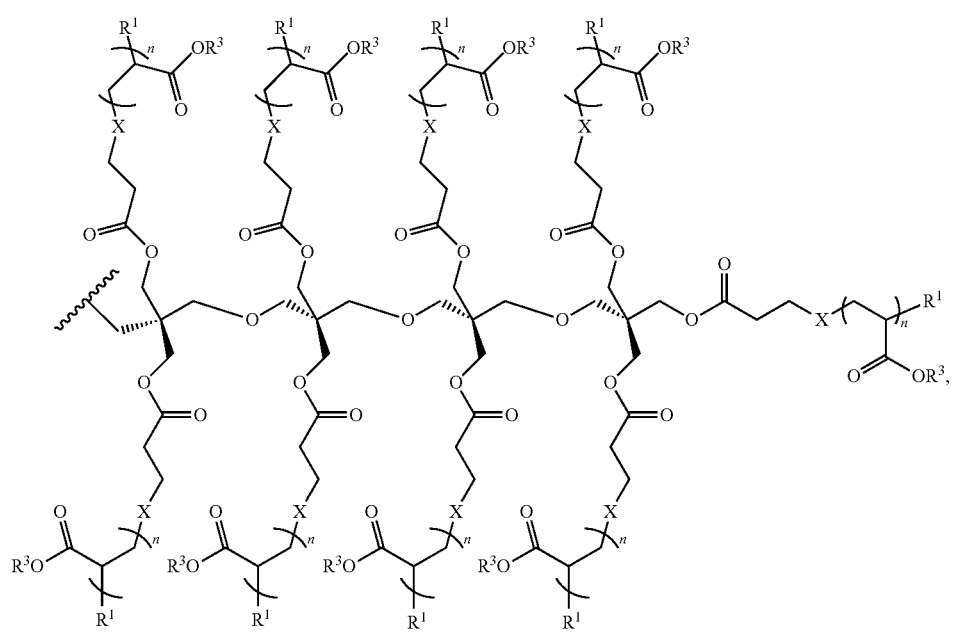

(IE)

structure according to Formula (IA), (IB), (IC), (ID), or (IE): wherein each substituent is as described above. In embodiments wherein $R^2$ is Formula (IA), the star-shaped is referred to as a 4-arm star-shaped polymer (4Star). In embodiments wherein $R^2$ is Formula (IB), the star-shaped is referred to as a 6-arm star-shaped polymer (6Star). In embodiments wherein $R^2$ is Formula (IC), the star-shaped is referred to as an 8-arm star-shaped polymer (8Star). In embodiments wherein $R^2$ is Formula (ID), the star-shaped is referred to as a 10-arm star-shaped polymer (10Star). In embodiments wherein $R^2$ is Formula (IE), the star-shaped is referred to as a 12-arm star-shaped polymer (12Star).

Thus, the star-shaped polymer according to the disclosure may have as few as three arms (where $R^2$ is H) and as many as 12 arms.

In embodiments, $R^2$ can be selected in view of the other formula parameters such that the star-shaped polymer, as a whole, remains substantially soluble in water. As described above, the ability of the polymer to bind to HAP, thereby repelling or preventing bacterial attachment while maintaining water-solubility is particularly advantageous for use the formulation, application, and use of an oral care composition according to the disclosure.

As provided herein, each n independently is 5 to 500, 10 to 400, or 15 to 300, for example 5, 10, 15, 20, 25, 50, 75, 100, 125, 150, 175, 200, 225, 250, 275, 300, 325, 350, 375, 400, 425, 450, 475 or 500.

In some embodiments, the star-shaped polymer has a structure selected from the group consisting of Formula (II), (III), (IV), (V), (VI), (VII), (VIII), (IX), (X), (XI), and (XII):

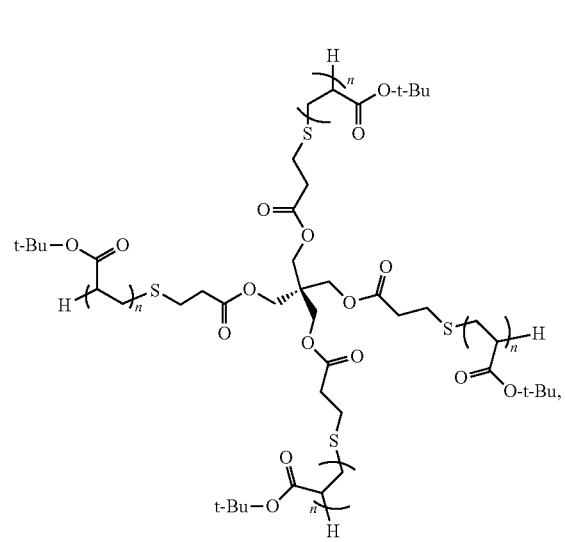
(II)
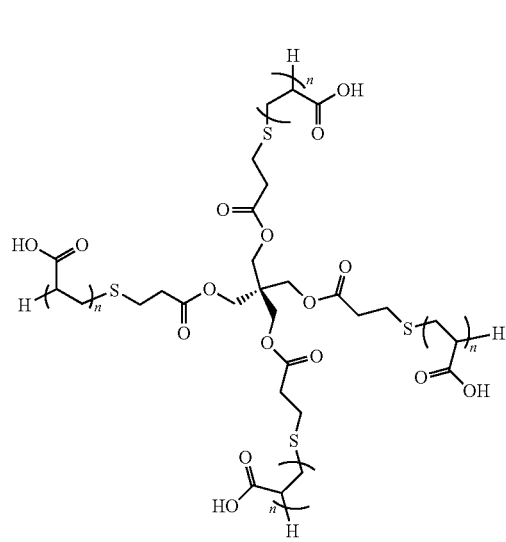
(III)
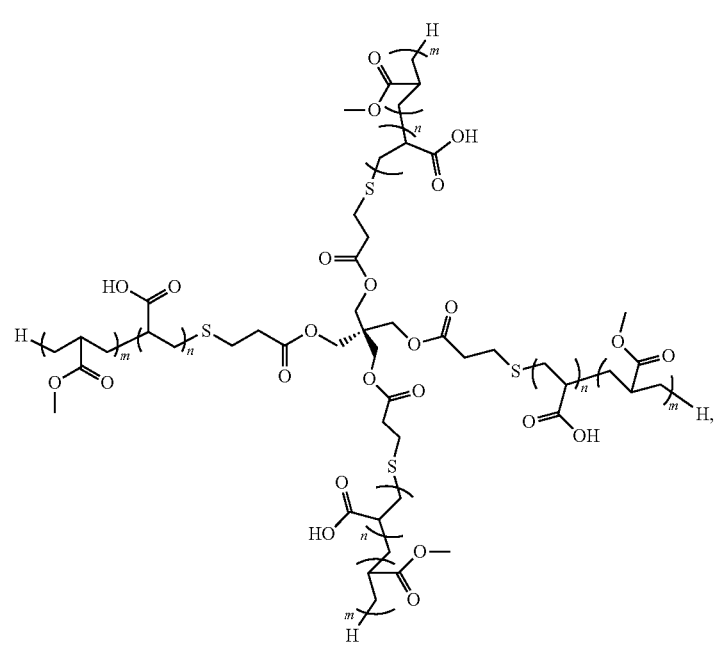
(IV)

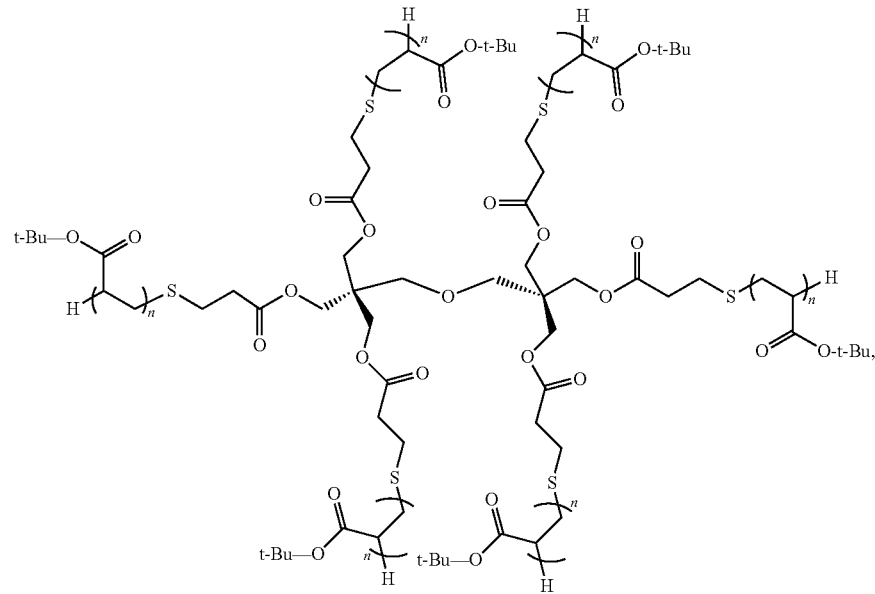
(V)
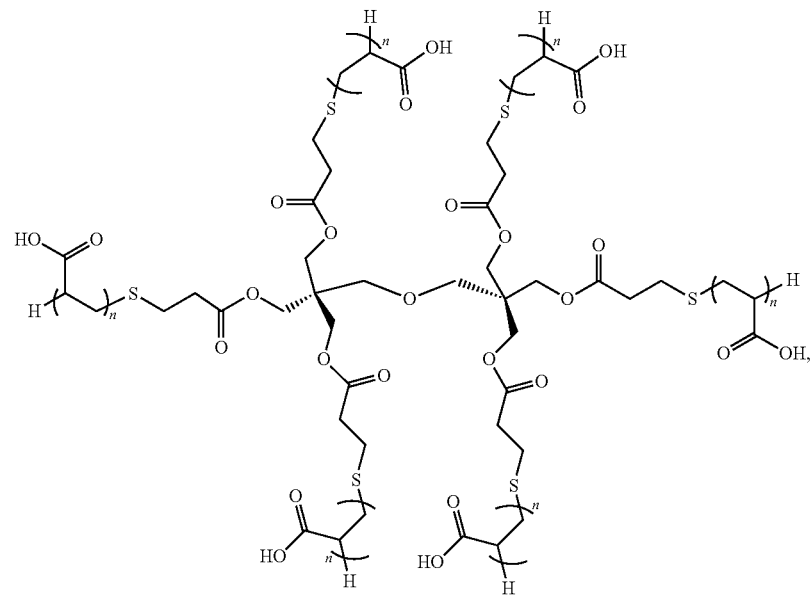
(VI)

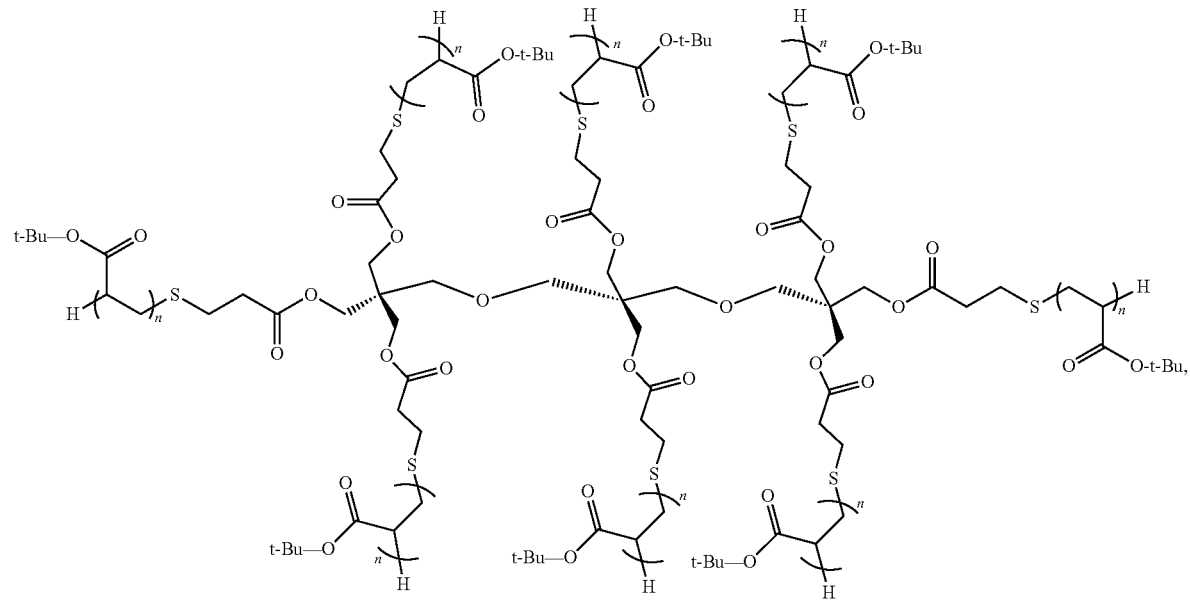
(VII)
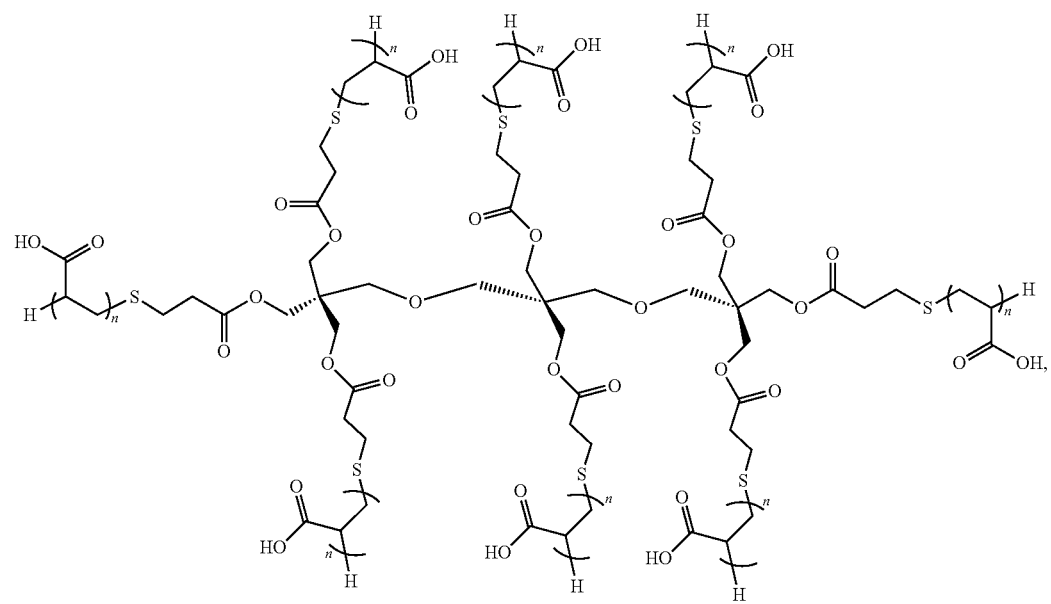
(VIII)

-continued
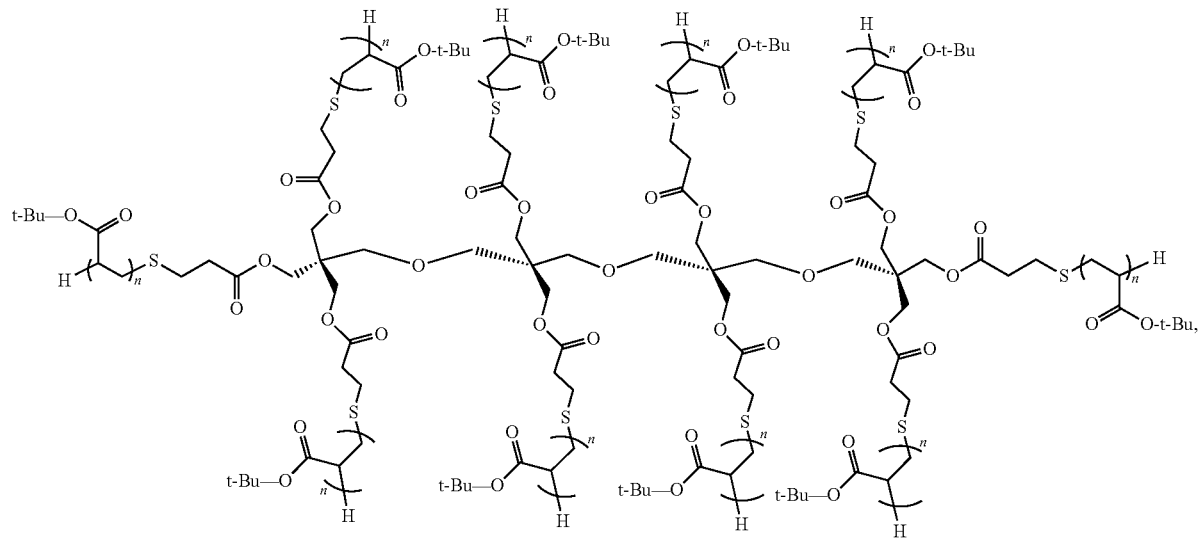
(IX)
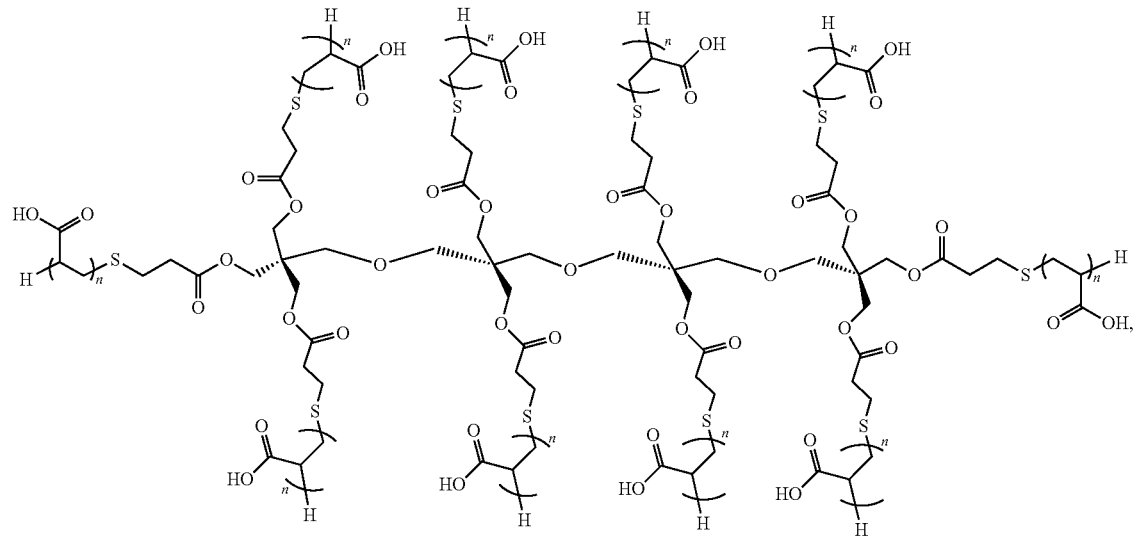
(X)
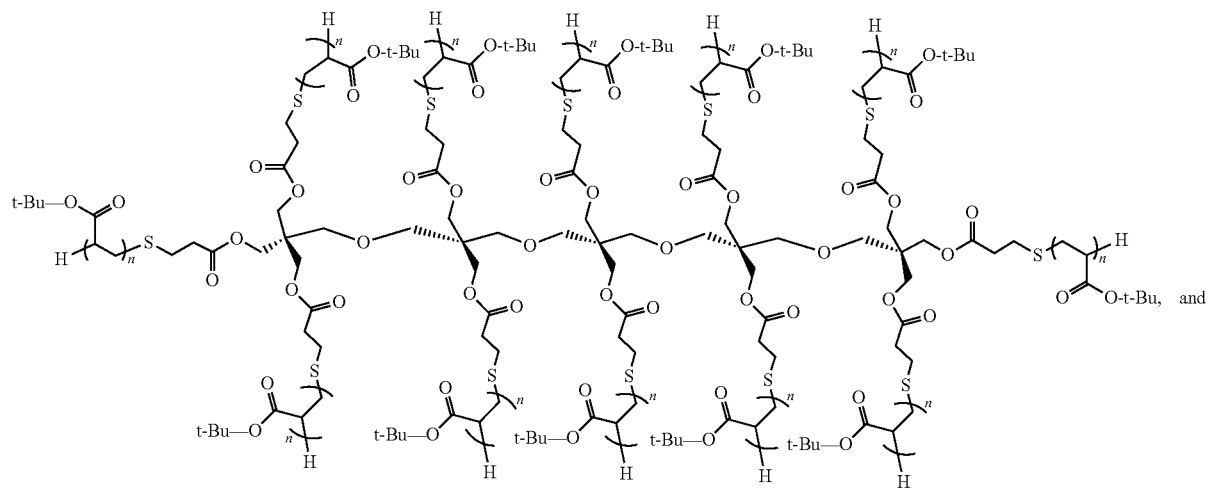
(XI)

(XII)

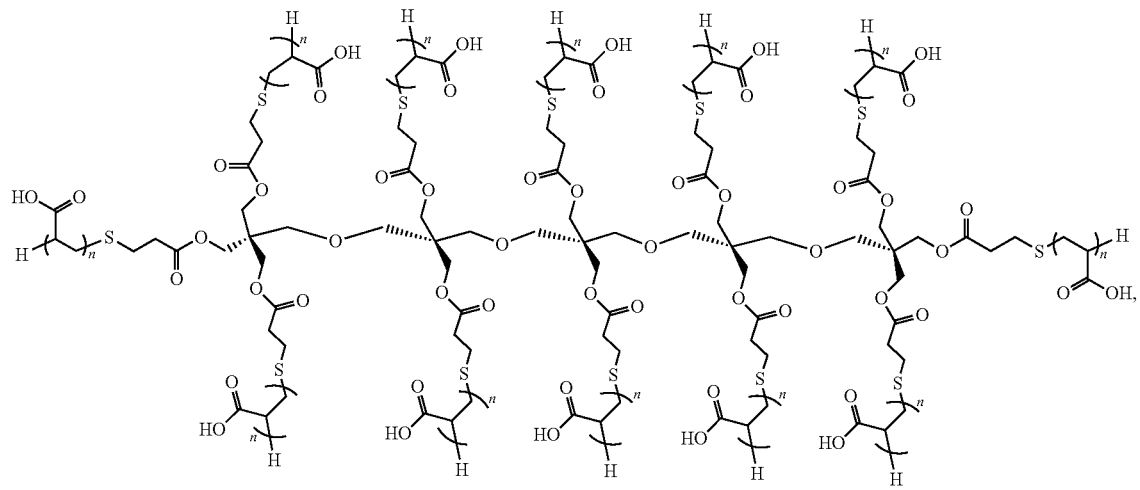

wherein each n and each m are independently in a range of 5 to 500, 10 to 400, or 15 to 300, for example 5, 10, 15, 20, 25, 50, 75, 100, 125, 150, 175, 200, 225, 250, 275, 300, 325, 350, 375, 400, 425, 450, 475 or 500.

The molecular weight of the star-shaped polymer is not particularly limited. In embodiments, the number average molecular weight ($M_n$) of the polymer ranges from about 1,000 g/mol to about 700,000 g/mol, about 1500 g/mol to about 500,000 g/mol, about 1750 g/mol to about 250,000 g/mol, or about 2000 g/mol to about 200,000 g/mol, for example about 1000, 1250, 1500, 1750, 2000, 2500, 3000, 3500, 4000, 4500, 5000, 6000, 7000, 8000, 9000, 10,000, 15,000, 20,000, 25,000, 30,000, 35,000, 40,000, 45,000, 50,000, 60,000, 70,000, 80,000, 90,000, 100,000, 125,000, 150,000, 175,000, 200,000, 225,000, 250,000, 275,000, 300,000, 325,000, 350,000, 375,000, 400,000, 425,000, 450,000, 475,000, 500,000, 525,000, 550,000, 575,000, 600,000, 625,000, 650,000, 675,000, or 700,000 g/mol The molecular weight of the star-shaped polymer can also be described by its weight average molecular weight ($M_w$). In embodiments, the weight average molecular weight ($M_w$) of the polymer ranges from about 1,000 g/mol to about 700,000 g/mol, about 1500 g/mol to about 500,000 g/mol, about 1750 g/mol to about 250,000 g/mol, or about 2000 g/mol to about 200,000 g/mol, for example about 1000, 1250, 1500, 1750, 2000, 2500, 3000, 3500, 4000, 4500, 5000, 6000, 7000, 8000, 9000, 10,000, 15,000, 20,000, 25,000, 30,000, 35,000, 40,000, 45,000, 50,000, 60,000, 70,000, 80,000, 90,000, 100,000, 125,000, 150,000, 175, 000, 200,000, 225,000, 250,000, 275,000, 300,000, 325,000, 350,000, 375,000, 400,000, 425,000, 450,000, 475,000, 500, 000, 525,000, 550,000, 575,000, 600,000, 625,000, 650,000, 675,000, or 700,000 g/mol. In embodiments, the weight average molecular weight of the polymer ranges from about 10,000 to about 150,000 g/mol.

The molecular weight of the star-shaped polymer can be adjusted by modifying the ratio of CTA to monomers. In general, as the ratio of CTA to monomers increases, the molecular weight of the star-shaped polymers decreases. The molar ratio of CTA to monomers can be in a range of about 1:1000 to about 1:20, for example about 1:500 to about 1:25, about 1:200 to about 3:100, or about 1:100 to about 1:50, such as, 1:1000, 1:500, 1:200, 1:100, 1:50, 3:100, 1:25, or 1:20.

The star-shaped polymer can be a hydrophobic star-shaped polymer having a content of hydrophobic monomers of at least about 5 mol %, 10 mol %, 15 mol %, 20 mol %, 25 mol % 30 mol %, about 40 mol %, about 45 mol %, about 50 mol %, about 55 mol %, or about 60 mol %. Suitable examples of hydrophobic monomers can include those described herein for the acrylate polymer, such as acrylic acid or its derivatives, methacrylic acid or its derivatives, and combinations of the foregoing. Acrylic acid derivatives include, but are not limited to, methyl acrylate, ethyl acrylate, butyl acrylate, sec-butyl acrylate, tert-butyl acrylate, and 2-ethylhexyl acrylate. Methacrylic acid derivatives include, but are not limited to methyl methacrylate, ethyl methacrylate, butyl methacrylate, sec-butyl methacrylate, tert-butyl methacrylate, and 2-ethylhexyl methacrylate.

The hydrophobic star-shaped polymer of the disclosure can have a water contact angle of at least about 60°, for example at least about 60°, 65°, 70°, 75° or 80° and/or up to about 95°, 90°, 85°, 80°, or 75°. A water contact angle of at least about 60° is generally desirable in that it has been found to correspond with the improved anti-bacterial properties of the star-shaped polymer. Methods of measuring the water contact angle, for example, on a hydroxyapatite surface, are generally known in the field of oral care, and are described in the examples provided herein.

The star-shaped polymer can be characterized by its dissociation constant ($K_d$) with HAP. In embodiments, the polymer has a $K_d$ of less than about 5 μmol/L, for example about 5 μmol/L, about 4.5 μmol/L, about 4 μmol/L, about 3.5 μmol/L, about 3 μmol/L, about 2.5 μmol/L, about 2 μmol/L, about 1.5 μmol/L, or about 1 μmol/L. Advantageously, the star-shaped polymers of the disclosure can have lower dissociation constants than corresponding linear polymers, which corresponds to improved binding to the hydroxyapatite surface.

The star-shaped polymer can be used in the oral care compositions, as described in more detail, below. In general, the star-shaped polymer can be used to inhibit bacterial attachment to a surface. Advantageously, the star-shaped polymers of the disclosure can effectively bind to hydroxyapatite. Accordingly, the star-shaped polymer of the disclosure can be used to inhibit bacterial attachment to a surface, wherein the surface comprises hydroxyapatite.

Oral Compositions

The star-shaped polymer as described herein can be used in oral compositions. The oral compositions according to the disclosure comprise the star-shaped polymer and an orally acceptable carrier.

The amount of the star-shaped polymer in the oral composition can range from about 0.1 wt % to about 10 wt %, based on the total weight of the composition. For example, the oral composition can comprise from about 0.5 wt % to about 7.5 wt %, about 1.0 wt % to about 5 wt %, about 0.5 wt % to about 4 wt %, about 0.5 wt % to about 3 wt %, about 0.5 wt % to about 2 wt %, about 1 wt % to about 10 wt %, about 1 wt % to about 7 wt %, about 1 wt % to about 6 wt %, or about 2 wt % to about 4 wt % star-shaped polymer, for example, about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, or 10 wt % star-shaped polymer, based on the total weight of the composition.

The oral composition further comprises an orally acceptable carrier. As used herein, "orally acceptable carrier" refers to a material or a combination of materials that are safe for use in oral compositions, commensurate with a reasonable risk/benefit ratio. The term "orally acceptable carrier" also refers to any vehicle useful in formulating any of the oral care compositions as described herein. The orally acceptable carrier is not harmful to a mammal in amounts disclosed herein when retained in the mouth, without swallowing, for a period sufficient to permit effective contact with a dental surface as required herein. In general, the orally acceptable carrier is not harmful even if unintentionally swallowed.

In embodiments, the oral composition comprises the star-shaped polymer and an orally acceptable carrier in a product such as a mouthwash, a mouth rinse, a dental cream, a toothpaste, a tooth gel, a periodontal gel, a tooth powder, a non-abrasive gel, a mousse, a foam, a mouth spray, a lozenge, a chewing gum, a dissolvable or non-dissolvable film or strip, a dental floss, an oral tablet, a dental implement, or a pet care product. In various embodiments, the oral composition according to the invention is not intentionally swallowed, but is rather retained in the oral cavity for a time sufficient to effect the intended utility. In other portable embodiments (such as a lozenge, mint, bead, wafer, liquid formulated for oral application from a small portable nebulizer, liquid formulated for oral application from a small portable drop-generating bottle, or a soft pliable tablet), the oral composition is intentionally swallowed, optionally after retention in the oral cavity for a time sufficient to effect intended utility.

Suitable orally acceptable carriers include, for example, water, aqueous co-solvents, a thickener, a buffer, a humectant, a surfactant, an abrasive, a sweetener, a mouth-feel agent, a flavorant, a colorant, an anti-caries agent, an antibacterial or antimicrobial agent, an anti-plaque agent, a cleaning agent, an adhesion agent, a foam modulator, a whitening agent, a tartar control (anticalculus) agent, a saliva stimulating agent, an antisensitivity or desensitizing agent, an antioxidant, a nutrient, a preservative, an enzyme, or any combination thereof. Typically, the carrier provides the composition with desired properties for maintaining or promoting contact with the enamel layer and/or otherwise allowing the star-shaped polymers to contact, coat, and/or adsorb to the enamel layer.

In embodiments, the oral care composition comprises water. Water employed in the preparation of the oral care compositions disclosed herein should be deionized and free of organic impurities. Water can make up the balance of the oral care composition. In some embodiments, the oral care compositions disclosed herein comprise up to about 90 wt % water, about 0.1 wt % to about 90 wt %, about 1 wt % to about 80 wt % about 2 wt % to about 70 wt %, about 5 wt % to about 60 wt %, about 5 wt % to about 50 wt % water, about 20 wt % to about 60 wt %, or about 10 wt % to 40 wt % water, based on the total weight of the composition. This amount of water includes the free water which is added plus that amount which is introduced with other components of the oral care composition, such as with sorbitol (which can be provided, for example, as a 70% active solution, the balance including water).

A thickener provides a desirable consistency and/or stabilizes and/or enhances performance (e.g., provides desirable active release characteristics upon use) of the oral care composition. Suitable thickeners for use in the oral compositions of the disclosure include, but are not limited to, carboxyvinyl polymers, carrageenan (also known as carrageenan gum), hydroxyethyl cellulose (HEC), natural and synthetic clays (e.g., Veegum and laponite), water soluble salts of cellulose ethers (e.g., sodium carboxymethylcellulose (CMC) and sodium carboxymethyl hydroxyethyl cellulose), natural gums (e.g., gum karaya, xanthan gum, gum arabic, and gum tragacanth), colloidal magnesium aluminum silicate, silica (e.g., finely divided silica), polyvinyl pyrrolidone, carbowaxes, fatty acids and salts thereof, and mixtures thereof. In some embodiments, the oral care compositions disclosed herein comprise from about 0.01 wt % to about 15 wt %, about 0.1 wt % to about 15 wt %, about 0.1 wt % to about 10 wt %, about 0.1 wt % to about 5 wt %, about 0.5 wt % to about 10 wt %, about 0.5 wt % to about 5 wt %, about 1 wt % to about 4 wt %, about 2 wt % to about 5 wt %, about 2 wt % to about 4 wt % or about 3 wt % to about 4 wt % thickener, based on the total weight of the composition. Higher weight percentages may be used for chewing gums, lozenges and breath mints, sachets, non-abrasive gels and subgingival gels. In some embodiments, a mixture of thickening silica and carrageenan gum is used as the thickener in the oral care compositions disclosed herein. In some embodiments, the oral care compositions disclosed herein comprise from about 0.01 wt % to about 15 wt %, about 0.1 wt % to about 15 wt %, about 0.1 wt % to about 10 wt %, about 0.1 wt % to about 5 wt %, about 0.5 wt % to about 10 wt %, about 0.5 wt % to about 5 wt %, about 1 wt % to about 4 wt %, about 2 wt % to about 5 wt %, about 2 wt % to about 4 wt %, or about 3 wt % to about 4 wt % thickening silica and carrageenan gum, based on the total weight of the composition.

A buffer adjusts the pH of oral care compositions, for example, to a range of about pH 4.0 to about pH 6.0. Buffers that can be used in the oral care compositions disclosed herein include, but are not limited to, sodium bicarbonate, sodium phosphate (e.g., monosodium phosphate ($NaH_2PO_4$), disodium phosphate ($Na_2HPO_4$), trisodium phosphate ($Na_3PO_4$)), sodium hydroxide, sodium carbonate, sodium acid pyrophosphate, citric acid, sodium citrate, and mixtures thereof. In some embodiments, the oral care compositions disclosed herein comprise from about 0.5 wt % to about 10 wt %, about 0.5 wt % to about 5 wt %, about 0.5 wt % to about 4 wt %, about 0.5 wt % to 3 wt %, about 0.5 wt % to 2 wt %, or about 1 wt % to about 2 wt % buffer, based on the total weight of the composition. In some embodiments, sodium hydroxide is used as the buffer in the oral care compositions disclosed herein. In some embodiments, the oral care compositions disclosed herein comprise from about 0.5 wt % to about 10 wt %, about 0.5 wt % to about 5 wt % of sodium hydroxide, about 0.5 wt % to about 4 wt %, about 0.5 wt % to about 3 wt %, about 0.5 wt % to about 2 wt %, or about 1 wt % to 2 wt % sodium hydroxide.

A humectant keeps oral care compositions from hardening upon exposure to air. Certain humectants can also impart desirable sweetness or flavor to oral care compositions. Humectants that may be used in the oral care compositions disclosed herein include, but are not limited to, glycerin, sorbitol, xylitol, butylene glycol, polyethylene glycol, propylene glycol, trimethyl glycine, and mixtures thereof. In some embodiments, the oral care compositions disclosed herein comprise up to about 70 wt % humectant, based on the total weight of the composition, for example, from about 10 wt % to about 70 wt %, about 10 wt % to about 65 wt %, about 10 wt % to about 60 wt %, about 10 wt % to about 50 wt %, about 20 wt % to about 50 wt %, about 30 wt % to about 50 wt %, or about 40 wt % to about 50 wt % humectant, based on the total weight of the composition. In some embodiments, a mixture of glycerin, sorbitol, and propylene glycol is used as the humectant in the oral care compositions disclosed herein. In some embodiments, the oral care compositions disclosed herein comprise up to about 70 wt % of glycerin, sorbitol, and propylene glycol, for example, from about 10 wt % to about 70 wt %, about 10 wt % to about 65 wt %, about 10 wt % to about 60 wt %, about 10 wt % to about 50 wt %, about 20 wt % to about 50 wt %, about 30 wt % to about 50 wt %, or about 40 wt % to about 50 wt % of glycerin, sorbitol, and propylene glycol.

In some embodiments, the oral care compositions disclosed herein comprise a surfactant. The surfactant can be selected from anionic, cationic, zwitterionic, and nonionic surfactants, and mixtures thereof. In some embodiments, the surfactant is reasonably stable throughout a wide pH range. Surfactants are described in, for example, U.S. Pat. No. 3,959,458, to Agricola et al; U.S. Pat. No. 3,937,807, to Haefele; and U.S. Pat. No. 4,051,234, to Gieske et al. In some embodiments, the oral care compositions disclosed herein comprise from about 0.01 wt % to about 10 wt %, about 0.05 wt % to about 5 wt %, about 0.1 wt % to about 10 wt %, about 0.1 to about 5 wt %, about 0.1 to about 2 wt %, or about 0.5 wt % to about 2 wt % of a surfactant, based on the total weight of the composition.

In some embodiments, the oral care compositions disclosed herein comprise an anionic surfactant. Anionic surfactants that may be used in the oral care compositions disclosed herein include, but are not limited to, (i) water-soluble salts of higher fatty acid monoglyceride monosulfates, such as the sodium salt of the monosulfated monoglyceride of hydrogenated coconut oil fatty acids such as sodium N-methyl N-cocoyl taurate, sodium cocomonoglyceride sulfate; (ii) higher alkyl sulfates, such as sodium lauryl sulfate; (iii) higher alkyl-ether sulfates, e.g., of formula $CH_3(CH_2)_mCH_2(OCH_2CH_2)_nOSO_3X$, wherein m is 6-16 (e.g., 10), n is 1-6 (e.g., 2, 3 or 4), and X is Na or K, for example sodium laureth-2 sulfate $(CH_3(CH_2)_{10}CH_2(OCH_2CH_2)_2OSO_3Na)$; (iv) higher alkyl aryl sulfonates such as sodium dodecyl benzene sulfonate (sodium lauryl benzene sulfonate); and (v) higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate. As used herein, "higher alkyl" refers to 06-30 alkyl. In some cases, the oral care compositions disclosed herein comprise from about 0.01 wt % to about 10 wt %, about 0.05 wt % to about 5 wt %, about 0.1 wt % to about 10 wt %, about 0.1 wt % to about 5 wt %, about 0.1 to about 2 wt %, or about 0.5 wt % to about 2 wt % anionic surfactant, based on the total weight of the composition. In some embodiments, the anionic surfactant is a water soluble salt of alkyl sulfates having from 10 to 18 carbon atoms in the alkyl radical or a water soluble salt of sulfonated monoglycerides of fatty acids having from 10 to 18 carbon atoms. Sodium lauryl sulfate, sodium lauroyl sarcosinate, and sodium coconut monoglyceride sulfonates are examples of anionic surfactants of that type. In some embodiments, the oral care compositions disclosed herein comprise sodium lauryl sulfate, sodium ether lauryl sulfate, or a mixture thereof. In some embodiments, the oral care compositions disclosed herein comprise sodium lauryl sulfate. In some embodiments, the oral care compositions disclosed herein comprise from about 0.01 wt % to about 10 wt %, about 0.05 wt % to about 5 wt %, about 0.1 wt % to about 10 wt %, about 0.1 to about 5 wt %, about 0.1 to about 2 wt %, or about 0.5 wt % to about 2 wt % sodium lauryl sulfate, based on the total weight of the composition.

The compositions of the invention can comprise an abrasive useful, for example, as a polishing agent. Any orally acceptable abrasive can be used, but type, fineness, (particle size) and amount of abrasive should be selected so that tooth enamel is not excessively abraded in normal use of the composition. Suitable abrasives include, but are not limited to, silica, for example in the form of precipitated silica or as admixed with alumina, insoluble phosphates, calcium carbonate, and mixtures thereof. Among insoluble phosphates useful as abrasives are orthophosphates, polymetaphosphates and pyrophosphates. Illustrative examples are dicalcium orthophosphate dihydrate, calcium pyrophosphate, calcium pyrophosphate, tricalcium phosphate, calcium polymetaphosphate and insoluble sodium polymetaphosphate. Some embodiments provide oral care compositions comprising from about 5 to about 15 wt % abrasive, based on the total weight of the composition. When abrasives are present, the average particle size is generally about 0.1 to about 30 microns, for example about 1 to about 20 or about 5 to 15 microns.

In some embodiments, the oral care compositions disclosed herein comprise a sweetener. Sweeteners that may be used in the oral care compositions disclosed herein include, but are not limited to, sucrose, glucose (i.e. dextrose), ribose, galactose, saccharin, sucralose, polydextrose, lactose, mannose, mannitol, sorbitol, erythritol, fructose (i.e. levulose), maltose, maltitol, xylose, xylitol, isomalt, saccharin salts (e.g., sodium saccharin), thaumatin, aspartame, D-tryptophan, dihydrochalcones, acesulfame, neotame, cyclamate salts, dextrin, dried invert sugar, corn syrup, partially hydrolyzed starch, hydrogenated starch hydrolysate, dipeptide-based intense sweeteners, and mixtures thereof. In some embodiments, the oral care compositions disclosed herein comprise from about 0.005 to about 10 wt %, about 0.01 wt % to about 10 wt %, about 0.1 wt % to about 10 wt %, about 0.1 wt % to about 5 wt %, about 0.1 wt % to about 3 wt %, about 0.1 wt % to about 1 wt %, or about 0.1 wt % to 0.5 wt % of a sweetener, based on the total weight of the composition. In some embodiments, sodium saccharin is used as the sweetener in the oral care compositions disclosed herein. In some embodiments, the oral care compositions disclosed herein about 0.005 wt % to about 10 wt %, about 0.01 wt % to about 10 wt %, about 0.1 wt % to about 10 wt %, about 0.1 wt % to about 5 wt %, about 0.1 wt % to about 3 wt %, about 0.1 wt % to about 1 wt %, or about 0.1 wt % to 0.5 wt % sodium saccharin, based on the total weight of the composition. Some components, such as sorbitol, can be included in amounts sufficient to serve the purpose of acting as a sweetener and as a humectant. In general, when provided in the relatively greater amounts suitable for a humectant, the sorbitol will also be present in an amount sufficient to act as a sweetener in the composition.

Flavoring agents, or flavorants, among those useful herein include any material or mixture of materials operable to enhance the taste of the composition. Any orally acceptable natural or synthetic flavorant can be used, such as flavoring oils, flavoring aldehydes, esters, alcohols, similar materials, and combinations thereof. Flavorants include vanillin, sage, marjoram, parsley oil, spearmint oil, cinnamon oil, oil of wintergreen (methylsalicylate), peppermint oil, clove oil, bay oil, anise oil, *eucalyptus* oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants, and mixtures thereof. Also encompassed within flavorants herein are mouth-feel agents. Mouth-feel agents include materials imparting a desirable texture or other feeling during use of the composition. Ingredients that can provide fragrance and/or other sensory effect in the mouth, including cooling or warming effects, include, but are not limited to, menthol, menthyl acetate, menthyl lactate, camphor, *eucalyptus* oil, eucalyptol, anethole, eugenol, *cassia*, oxanone, [alpha]-irisone, propenyl guaiethol, thymol, linalool, benzaldehyde, cinnamaldehyde, N-ethyl-p-menthan-3-carboxamine, N,2,3-trimethyl-2-isopropylbutanamide, 3-1-menthoxypropane-1,2-diol, cinnamaldehyde glycerol acetal (CGA), methone glycerol acetal (MGA), and mixtures thereof. One or more flavorants can be present in a total amount of about 0.01 wt % to about 5 wt %, about 0.05 to about 2 wt %, about 0.1 wt % to about 2.5 wt %, or about 0.1 to about 0.5 wt % flavorant, based on the total weight of the composition.

In some embodiments, the oral care compositions disclosed herein comprise colorants or coloring agents, including but not limited to, pigments, dyes, speckles, beads, strips, pearling agents, and mixtures thereof. These colorants can impart a particular luster or reflectivity to the oral surface, or to the oral composition itself. In various embodiments, colorants are operable to provide a white or light-colored coating on a dental surface, to act as an indicator of locations on a dental surface that have been effectively contacted by the oral composition, and/or to modify appearance, in particular color and/or opacity, of the oral composition to enhance attractiveness to the consumer. Any orally acceptable colorant can be used, including FD&C dyes and pigments, talc, mica, magnesium carbonate, calcium carbonate, magnesium silicate, magnesium aluminum silicate, silica, titanium dioxide, zinc oxide, red, yellow, brown and black iron oxides, ferric ammonium ferrocyanide, manganese violet, ultramarine, titaniated mica, bismuth oxychloride, and mixtures thereof. One or more colorants can be present in a total amount of about 0.001 wt % to about 20 wt %, for example about 0.01 wt % to about 10 wt % or about 0.1 wt % to about 5 wt %, based on the total weight of the composition.

In some embodiments, the oral care compositions disclosed herein comprise an anti-caries agent. In some embodiments, the oral care compositions disclosed herein comprise from about 0.001 wt % to about 10 wt %, about 0.01 wt % to about 10 wt %, about 0.01 wt % to about 5 wt %, about 0.01 wt % to about 1 wt %, about 0.01 wt % to about 0.3 wt %, about 0.1 wt % to about 5 wt %, about 0.1 wt % to about 2 wt %, about 0.1 wt % to about 1 wt %, about 0.1 wt % to about 0.8 wt %, about 0.1 wt % to about 0.6 wt %, about 0.1 wt % to about 0.5 wt %, or about 0.1 wt % to about 0.3 wt % of the anti-caries agent, based on the total weight of the composition. In some embodiments, the anti-caries agent is a fluoride ion source. In some embodiments, the oral care compositions disclosed herein comprise 0.001 wt % to about 10 wt %, about 0.01 wt % to about 10 wt %, about 0.01 wt % to about 5 wt %, about 0.01 wt % to about 1 wt %, about 0.01 wt % to about 0.3 wt %, about 0.1 wt % to about 5 wt %, about 0.1 wt % to about 2 wt %, about 0.1 wt % to about 1 wt %, about 0.1 wt % to about 0.8 wt %, about 0.1 wt % to about 0.6 wt %, about 0.1 wt % to about 0.5 wt %, or about 0.1 wt % to about 0.3 wt % fluoride ion source, based on the total weight of the composition. Examples of fluoride ion sources that may be used in the oral compositions disclosed herein can be found in U.S. Pat. No. 3,535,421 to Briner et al.; U.S. Pat. No. 4,885,155 to Parran, Jr. et al., and U.S. Pat. No. 3,678,154 to Widder et al. Other examples of fluoride ion sources include, but are not limited to, stannous fluoride, sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and combinations thereof. In some embodiments, the fluoride ion source includes stannous fluoride, sodium fluoride, and sodium monofluorophosphate, as well as mixtures thereof. In some embodiments, the anti-caries agent comprises sodium fluoride. In some embodiments, the oral care compositions disclosed herein 0.001 wt % to about 10 wt %, about 0.01 wt % to about 10 wt %, about 0.01 wt % to about 5 wt %, about 0.01 wt % to about 1 wt %, about 0.01 wt % to about 0.3 wt %, about 0.1 wt % to about 5 wt %, about 0.1 wt % to about 2 wt %, about 0.1 wt % to about 1 wt %, about 0.1 wt % to about 0.8 wt %, about 0.1 wt % to about 0.6 wt %, about 0.1 wt % to about 0.5 wt %, or about 0.1 wt % to about 0.3 wt % sodium fluoride, based on the total weight of the composition.

In some embodiments, the oral care compositions disclosed herein comprise the anti-caries agent which is a fluoride ion source in an amount sufficient to supply from about 25 ppm to about 25,000 ppm, about 100 ppm to about 20,000 ppm, about 300 ppm to about 15,000 ppm, about 500 ppm to about 10,000 ppm, about 500 ppm to about 8,000 ppm, about 500 ppm to about 6,000 ppm, about 500 ppm to about 4,000 ppm, about 500 ppm to about 2,000 ppm, about 500 ppm to about 1,800 ppm, or about 1000 ppm to about 1600 ppm fluoride ions, for example, about 1450 ppm of fluoride ions. The appropriate level of fluoride ions will depend on the particular application. It is to be understood that the weights of fluoride salts to provide the appropriate level of fluoride ion will vary based on the weight of the counter ion in the salt, and one of skill in the art may readily determine such amounts. In some embodiments, a toothpaste for consumer use comprises the anti-caries agent which is a fluoride ion source in an amount sufficient to supply from about 1,000 ppm to about 1,500 ppm of fluoride ions, with pediatric toothpastes having somewhat less. In some embodiments, a dentifrice or coating for professional application comprises the anti-caries agent which is a fluoride ion source in an amount sufficient to supply from about 5,000 ppm to about 25,000 ppm of fluoride ions.

In some embodiments, the oral care compositions disclosed herein comprise an anti-bacterial, or antimicrobial, agent. Examples of anti-bacterial or antimicrobial agents that can be used in the oral compositions of the disclosure include, but are not limited to, halogenated diphenyl ether (e.g. triclosan), herbal extracts and essential oils (e.g., rosemary extract, tea extract, *magnolia* extract, magnolol, butyl magnolol, thymol, menthol, eucalyptol, geraniol, carvacrol, citral, hinokiol, propyl honokiol, catechol, methyl salicylate, epigallocatechin gallate, epigallocatechin, gallic acid, miswak extract, sea-buckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts, for example, zinc citrate, zinc lactate or zinc chloride; stannous salts, for example stannous chloride and stannous fluoride; copper salts; iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts, methyl hydroxybenzoate, and mixtures thereof. In some embodiments, the oral care compositions disclosed herein comprise from about 0.01 wt % to about 10 wt %, about 0.1 wt % to about 10 wt %, about 0.5 wt % to about 5 wt %, about 0.01 wt % to about 5 wt %, about 0.03 wt % to about 4 wt %, about 0.05 wt % to about 3 wt %, about 0.07 wt % to about 2 wt %, about 0.09 wt % to about 1 wt %, about 0.1 wt % to about 0.9 wt % about 0.1 wt % to about 0.8 wt %, about 0.1 wt % to about 0.7 wt %, about 0.1 wt % to about 0.6 wt % about 0.1 wt % to about 0.5 wt %, about 0.1 wt % to about 0.4 wt %, about 0.2 wt % to about 0.4 wt % of an anti-bacterial or antimicrobial agent, based on the total weight of the composition. The amount of the anti-bacterial agent will vary depending on the type of oral care composition, with levels used in dentifrice oral care compositions such as toothpaste being, for example, 5 to 15 times greater than those used in solution-based oral care compositions for coating enamel layers such as mouthwash. For example, a mouthwash comprising triclosan may comprise, for example, about 0.03 wt % triclosan, while a toothpaste comprising triclosan may comprise, for example, about 0.3 wt % triclosan. In some embodiments, the antimicrobial agent is selected from the group consisting of triclosan, cetyl pyridinium chloride, *magnolia* extract, magnolol, honokiol, butyl magnolol, propyl honokiol, zinc chloride, zinc lactate, zinc citrate, stannous fluoride, and stannous chloride. Some components, such as stannous fluoride, can be included in amounts sufficient to serve the purpose of acting as an anti-bacterial and an anti-caries agent. For example, stannous fluoride can be present in an amount ranging from about 0.01 wt % to about 1 wt %, and provide both anti-bacterial and anti-caries properties to the composition.

The oral composition can also include a tooth whitening or tooth bleaching agent. Suitable whitening and bleaching agents include peroxides, metal chlorites, and/or persulfates. Peroxides include hydroperoxides, hydrogen peroxide, peroxides of alkali and alkaline earth metals, organic peroxy compounds, peroxy acids, and mixtures thereof. Peroxides of alkali and alkaline earth metals include lithium peroxide, potassium peroxide, sodium peroxide, magnesium peroxide, calcium peroxide, barium peroxide, and mixtures thereof. Other peroxides include perborate, urea peroxide, and mixtures thereof. Suitable metal chlorites can include calcium chlorite, barium chlorite, magnesium chlorite, lithium chlorite, sodium chlorite, and potassium chlorite. Such agents may be added in effective amounts, e.g., from about 1 wt % to about 20 wt % by weight based on the total weight of the composition, depending on the agent chosen.

The compositions of the disclosure can also comprise a tartar control (anticalculus) agent. Tartar control agents among those useful herein include salts of any of these agents, for example their alkali metal and ammonium salts: phosphates and polyphosphates (for example pyrophosphates), polyaminopropanesulfonic acid (AMPS), polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and. Useful inorganic phosphate and polyphosphate salts include monobasic, dibasic and tribasic sodium phosphates, sodium tripolyphosphate, tetrapolyphosphate, mono-, di-, tri- and tetrasodium pyrophosphates, sodium trimetaphosphate, sodium hexametaphosphate and mixtures thereof. Other useful tartar control agents include polycarboxylate polymers and polyvinyl methyl ether/maleic anhydride (PVM/MA) copolymers, such as GANTREZ®. In some embodiments, the tartar control agent is a polycarboxylate polymer or a polyvinyl methyl ether/maleic anhydride (PVM/MA) copolymer.

The compositions of the disclosure can include a saliva stimulating agent useful, for example, in amelioration of dry mouth. Any orally acceptable saliva stimulating agent can be used, including, but not limited to, food acids such as citric, lactic, malic, succinic, ascorbic, adipic, fumaric and tartaric acids, and mixtures thereof. One or more saliva stimulating agents are optionally present in saliva stimulating effective total amount.

The compositions of the disclosure can include one or more desensitizing or antisensitivity agents, e.g., potassium salts such as potassium nitrate, potassium bicarbonate, potassium chloride, potassium citrate, and potassium oxalate; capsaicin; eugenol; strontium salts; zinc salts; chloride salts and combinations thereof. Such agents may be added in effective amounts, e.g., from about 1 wt % to about 20 wt %, based on the total weight of the composition, depending on the agent chosen. The oral compositions according to the disclosure may also be used to treat hypersensitivity by blocking dentin tubules when applied to a tooth.

In some embodiments, the oral compositions of the disclosure include an antioxidant. Any orally acceptable antioxidant can be used, including butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof.

In some embodiments, the compositions of the disclosure comprise a nutrient. Suitable nutrients include vitamins, minerals, amino acids, and mixtures thereof. Vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Nutritional supplements can include amino acids (such as L-tryptophan, L-lysine, methionine, threonine, levocarnitine and L-carnitine), lipotropics (such as choline, inositol, betaine, and linoleic acid), and mixtures thereof.

Suitable enzymes useful for the oral compositions of the disclosure are described in U.S. Pat. No. 7,939,306, which is incorporated by reference. These enzymes include protein substances within the class of proteases, which breakdown or hydrolyze proteins (proteases). These proteolytic enzymes are obtained from natural sources or by the action of microorganisms having a nitrogen source and a carbon source. Examples of proteolylic enzymes useful in the practice of the present invention include papain, bromelain, chymotrypsin, ficin and alcalase.

Papain obtained from the milky latex of the *Papaya* tree is a proteolytic enzyme suitable for use in the compositions of the disclosure and can be incorporated in the oral care composition in an amount of about 0.1 wt % to about 10 wt % or about 0.5 wt % to about 5 wt %, based on the total weight of the composition, such papain having an activity of 150 to 300 MCU per milligram as determined by the Milk Clot Assay Test of the Biddle Sawyer Group (see J. Biol. Chem., vol. 121, pages 737-745).

Another enzyme which can be included in the compositions of the disclosure is a carbohydrase. Suitable examples of carbohydrases include, but are not limited to, glucoamylase, alpha and beta-amylase, dextranase and mutanase. Glucoamylase is a saccharifying glucoamylase of *Aspergillus niger* origin cultivated by fermentation. This enzyme can hydrolyze both the alpha-D-1,6 glucosidic branch points and the alpha-1,4 glucosidic bonds of glucosyl oligosaccharides. The oral composition can include from about 0.001 wt % to about 2 wt % of the carbohydrase, or about 0.01 wt % to about 0.55 wt % of the carbohydrase, based on the total weight of the composition.

The compositions can also include lipase, such as plant lipase, gastric lipase, or pancreatic lipase. The lipase enzyme can be derived from a select strain of *Aspergillus niger*, exhibiting random cleaving of the 1,3 positions of fats and oils. The enzyme has maximum lipolytic activity at pH 5.0 to 7.0 when assayed with olive oil. The lipase can be included in the oral composition in an amount ranging from about 0.010 wt % to about 5.0 wt % or about 0.02 wt % to about 0.10 wt %, based on the total weight of the composition.

The presence of tannase enzyme can also be beneficial in facilitating the breakdown of extrinsic stain. Tannase enzymes have been purified from *Aspergillus niger* and *Aspergillus allianceus* and are useful in the hydrolysis of tannins, known to discolor the tooth surface.

Other suitable enzymes which can be included in the oral compositions of the disclosure include lysozyme, derived from egg white, which contains a single polypeptide chain crosslinked by four disulfide bonds having a molecular weight of 14,600 daltons. The enzyme can exhibit antibacterial properties by facilitating the hydrolysis of bacterial cell walls cleaving the glycosidic bond between carbon number 1 of N-acetylmurarnic acid and carbon number 4 of N-acetyl-D-glucosamine, which in vivo, are polymerized to form the cell wall polysaccharide. Additionally, pectinase, an enzyme that is present in most plants, facilitates the hydrolysis of the polysaccharide pectin into sugars and galacturonic acid.

In some embodiments, the enzyme is one or more enzymes selected from the group consisting of protease, carbohydrase, lipase, tannase, lysozyme, pectinase and combinations thereof. In some cases, the protease is selected from the group consisting of papain, bromelain, chymotrypsin, ficin, alcalase and combinations thereof. In some cases, the carbohydrase is selected from the group consisting of glucoamylase, alpha-amylase, beta-amylase, dextranase, mutanase and combinations thereof.

The compositions of the disclosure can also include other conventional agents often included in oral care compositions such as an anti-plaque agent, a cleaning agent, an adhesion agent, a foam modulator, a whitening agent (e.g., cleaning silica or a peroxide), or any combination thereof. Each of the anti-plaque agent, the cleaning agent, the adhesion agent, and the foam modulator can be included in any amount suitable for the oral composition in which it is present.

General Synthesis of Star-Shaped Polymers

The star-shaped polymers of the disclosure can be synthesized using conventional techniques and readily available starting materials known to those skilled in the art. In general, the compounds provided herein are conveniently obtained via standard organic and polymer chemistry synthesis methods. The following descriptions of synthetic methods are designed to illustrate, but not to limit, general procedures for the preparation of the polymers of the present disclosure.

In general, the star-shaped polymers of Formula (I) can be synthesized in line with the examples shown below. For example, the polymers can be prepared by the admixing of a monomer with a chain transfer agent (CTA) and a radical initiator (e.g. AIBN) in a suitable solvent (e.g. acetonitrile and/or DMF). The CTA can be appropriately selected to achieve a comparative linear polymer or a 3-arm, 4-arm, 6-arm, 8-arm, 10-arm, or 12-arm star-polymer. For example, to obtain a comparative linear polymer, the CTA can be methyl mercaptopropionate (MMP). To obtain a 4-star-shaped polymer, the CTA can be pentaerythritol tetrakis(3-mercaptopropionate) (PETMP). To obtain a 6-arm star-shaped polymer, the CTA can be dipentaerythritol hexakis (3-mercaptopropionate) (DPEHMP). The determination of suitable CTAs to prepare a 3-arm, 8-arm, 10-arm, and 12-arm star-shaped polymer would be within the purview of the person of ordinary skill in the art, in view of the foregoing description and following examples.

The monomer(s) used in the reaction is not limited and can be selected based on the desired properties of the final star-shaped polymer.

Methods of Use

The disclosure further provides methods of using the oral composition of the disclosure. The composition according to the disclosure may be administered to or applied to a human or other mammalian subject. The composition may be suitable for administration or application to the oral cavity of a human or mammalian subject. Typically, the composition can be used for inhibiting microbial biofilm formation and/or degrading microbial biofilm on an enamel layer.

In various embodiments, the disclosure provides methods of forming a layer on a tooth surface comprising administering to the subject an oral care composition according to the disclosure.

In various embodiments, the disclosure provides methods of inhibiting bacterial attachment to teeth comprising administering to the subject an oral care composition according to the disclosure. In particular, the star-shaped polymers of the disclosure have been found to effectively bind to HAP surfaces (e.g. the surfaces of teeth), thereby providing a protective layer and preventing and/or inhibiting the attachment of various bacteria to the HAP surfaces. Advantageously, the star-shaped polymers have shown increased binding affinity to HAP surfaces as compared to the comparative linear polymers. This is particularly surprising in view of the ability of the comparative linear polymers to more easily stretch across the HAP surface. Similarly, the star-shaped polymers of the disclosure surprisingly have been demonstrated to significantly reduce the attachment of bacteria such as *Actinomyces viscosus* and *Streptococcus oralis* to HAP surfaces.

In various embodiments, the disclosure provides the use of the star-shaped polymers in inhibiting bacterial attachment to a surface. In embodiments, the surface comprises hydroxyapatite (e.g. a tooth). In embodiments, the bacteria can comprise *Actinomyces viscosus* and/or *Streptococcus oralis*.

The foregoing description is given for clearness of understanding only, and no unnecessary limitations should be understood therefrom, as modifications within the scope of the disclosure may be apparent to those having ordinary skill in the art.

The oral compositions and methods in accordance with the disclosure can be better understood in light of the following examples, which are merely intended to illustrate the compositions and methods, and are not meant to limit the scope thereof in any way.

EXAMPLES

Materials 2,2'-azobisisobutyronitrile (AIBN) and pentaerythritol tetrakis(3-mercaptopropionate) (PETMP) were purchased from Sigma-Aldrich Co. LLC. Dipentaerythritol hexakis(3-mercaptopropionate) (DPEHMP) was purchased from TCI America. Methacryloxyethyl thiocarbamoyl rhodamine B was purchased from Polysciences. Trifluoroacetic acid (TFA) and solvents were purchased from Thermo Fisher Scientific, Inc. Tert-butyl acrylate (t-BuA), methyl acrylate, and methyl mercaptopropionate (MMP) were purchased from Acros Organics. The inhibitors of these monomers were removed by passing through alumina before use. Other chemicals and solvents were used without further purification. $^1$H NMR was performed using a Varian MR400 (400 MHz) and analyzed using VNMRJ 3.2 and MestReNova. Gel permeation chromatography (GPC) analysis was performed using a Waters 1515 HPLC instrument using THF as an eluent, equipped with Waters Styragel (7.8×300 mm) HR 0.5, HR 1, and HR 4 columns in sequence and detected by a differential refractometer (RI). Sintered HAP discs (0.5 cm in diameter) were purchased from Himed, Inc.

Example 1: Synthesis of Polymers

Synthesis of t-butyl poly(acrylic acid) (tBu PAA) homopolymers

Tert-Butyl acrylate (t-BuA), AIBN, and chain transfer agent (CTA) (MMP, PETMP, or DPEHMP) in acetonitrile were mixed in a flask under the conditions provided in Table 1, below. To prepare a comparative linear polymer, MMP was used as the CTA. To prepare a 4-arm star-shaped polymer, PETMP was used as the CTA. To prepare a 6-arm star-shaped polymer, DPEHMP was used as the CTA. Oxygen was removed by nitrogen gas bubbling for 10 minutes, and the solution was stirred at 70° C. for 16 hours. The reaction was cooled to room temperature. The solvent was removed by evaporation under reduced pressure. The resultant residue was dissolved in diethyl ether, and the polymer was isolated by precipitation in a methanol:water [50:50 (v/v)] mixture. The polymer arm length (DP) was calculated by comparing integrated peaks of —OCH$_2$— group of chain transfer agent to the —CH— polymer backbone. The number average molecular weight ($M_e$) was calculated using the DP and molecular weights of monomers and CTAs. Gel permeation chromatography molecular mass results were determined using a calibration curve based on standard samples of polystyrene. $^1$H NMR (CDCl$_3$, 400 MHz) δ: 4.21-4.06 (s, 2H, —OCH$_2$— of PETMP), 2.85-2.51 (brs, 4H, —SCH$_2$CH$_2$—), 2.37-2.07 (brs, 1H, —CH—), 1.97-1.14 (brs, 11H, —CH$_3$ and —CH$_2$—).

The t-butyl groups of polymers were then removed by the addition of trifluoroacetic acid (TFA) (5 mL to 1 g of polymer). After stirring for 30 min, TFA was removed by blowing with nitrogen gas. The residue was dissolved in methanol, and deprotected polymers were isolated by precipitating in excess diethyl ether. Subsequently, the precipitate was dissolved in distilled water and lyophilized to yield the desired product. $^1$H NMR (DMSO, 400 MHz) 2.4-2.0 (brs, 1H, —CH—), 1.8-1.2 (brs, 2H, —CH$_2$—).

The synthesis of star-shaped polymers generally followed the following scheme; while the 4-arm star shaped polymer scheme is shown, other substantially similar schemes using substantially similar reactants can be used to synthesize star-shaped polymers having different numbers of arms, different chain lengths, etc.:

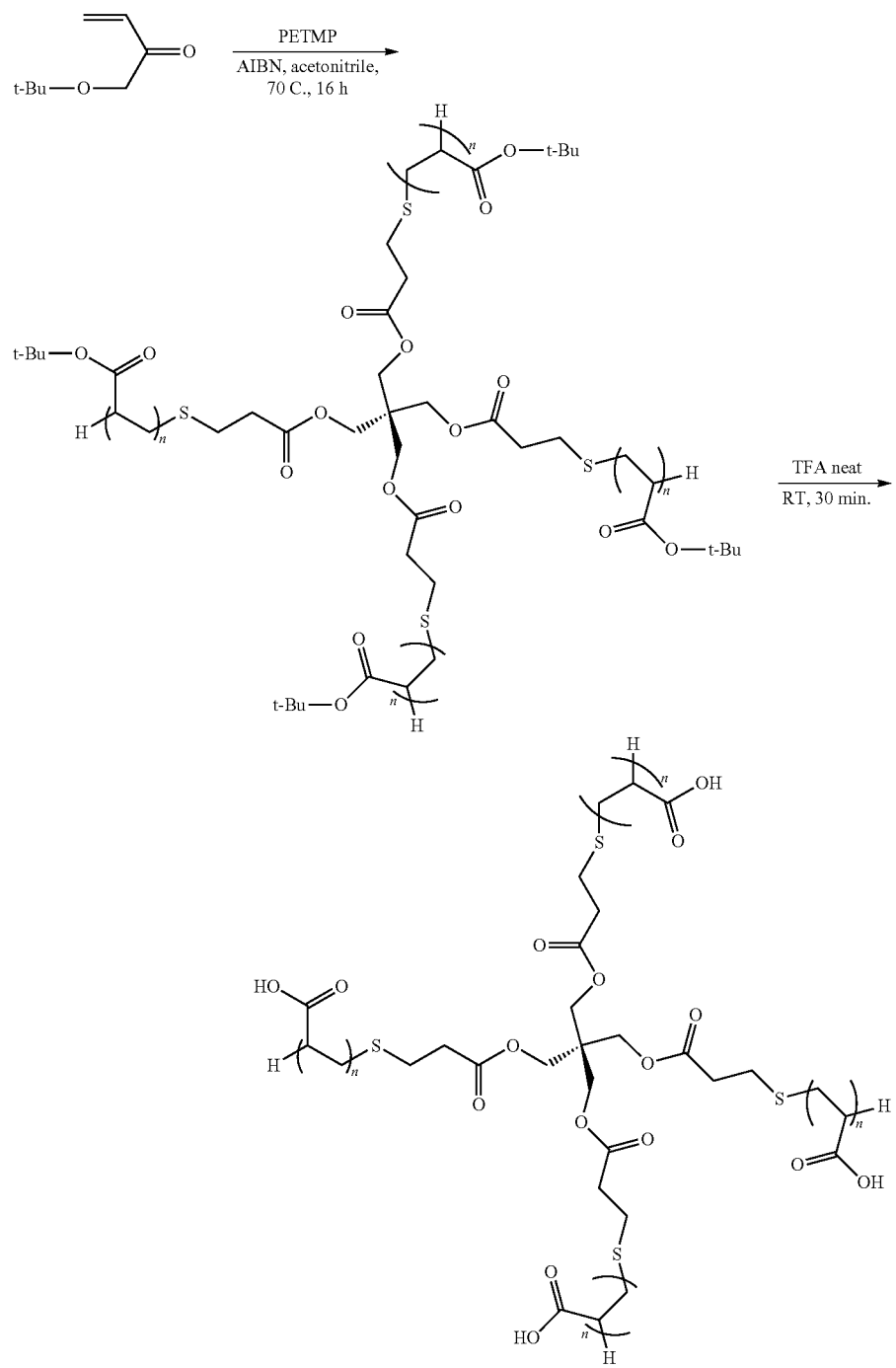
| | Polymerization conditions for tBu PAA homopolymers | | | | | | |
|---|---|---|---|---|---|---|---|
| Polymer[†] | t-BuA (g) | t-BuA (mmol.) | CTA (g) | CTA (mmol.) | AIBN (g)/ (mmol.) | AIBN (mmol.) | MeCN (g) |
| Lin-27 | 10 | 78.02 | 0.421 | 0.868 | 0.143 | 0.868 | 20 |
| Lin-151 | 10 | 78.02 | 0.060 | 0.126 | 0.021 | 0.126 | 20 |
| Lin-323 | 10 | 78.02 | 0.024 | 0.05 | 0.008 | 0.050 | 20 |
| LinPAA-238 | 5.0 | 39.01 | 0.032 | 0.039 | 0.006 | 0.039 | 10 |
| LinPAA-253 | 20 | 156.04 | 0.130 | 1.56 | 0.256 | 1.560 | 40 |
| Lin[‡] | 5.0 | 39.01 | 0.006 | 0.039 | 0.006 | 0.039 | 10 |
| Lin-211 | 5 | 39.01 | 0.024 | 0.201 | 0.027 | 0.039 | 10 |
| Lin-16 | 2.0 | 15.60 | 0.125 | 0.156 | 0.026 | 0.156 | 4 |

TABLE 1-continued

Polymerization conditions for tBu PAA homopolymers

| Polymer[†] | t-BuA (g) | t-BuA (mmol.) | CTA (g) | CTA (mmol.) | AIBN (g)/ (mmol.) | AIBN (mmol.) | MeCN (g) |
|---|---|---|---|---|---|---|---|
| Lin-37 | 2.0 | 15.60 | 0.038 | 0.156 | 0.026 | 0.156 | 4 |
| Lin-132 | 2.0 | 15.60 | 0.012 | 0.156 | 0.026 | 0.156 | 4 |
| 4Star-5 | 1.0 | 7.802 | 0.152 | 0.3109 | 0.013 | 0.078 | 2 |
| 4Star-8 | 1.0 | 7.802 | 0.094 | 0.1917 | 0.008 | 0.0479 | 2 |
| 4Star-11 | 1.0 | 7.802 | 0.068 | 0.1386 | 0.006 | 0.0347 | 2 |
| 4Star-13 | 1.0 | 7.802 | 0.056 | 0.1138 | 0.005 | 0.0285 | 2 |
| 4Star-16 | 1.0 | 7.802 | 0.046 | 0.0935 | 0.004 | 0.0234 | 2 |
| 4Star-21 | 1.0 | 7.802 | 0.053 | 0.108 | 0.004 | 0.027 | 2 |
| 4Star-4 | 10.0 | 78.02 | 2.425 | 4.962 | 0.204 | 1.241 | 20 |
| 4Star-39 | 10.0 | 78.02 | 0.312 | 0.639 | 0.026 | 0.16 | 20 |
| 4Star-130 | 10.0 | 78.02 | 0.123 | 0.252 | 0.010 | 0.063 | 20 |
| 4Star-18 | 5.0 | 39.01 | 0.257 | 0.525 | 0.064 | 0.390 | 10 |
| 4Star-165 | 5.0 | 39.01 | 0.024 | 0.05 | 0.064 | 0.390 | 10 |
| 4Star-196 | 20.0 | 156.04 | 0.098 | 0.2 | 0.256 | 1.560 | 40 |
| 6Star-3 | 10.0 | 78.02 | 3.535 | 4.515 | 0.185 | 1.128 | 20 |
| 6Star-21 | 10.0 | 78.02 | 0.407 | 0.52 | 0.021 | 0.13 | 20 |
| 6Star-24 | 10.0 | 78.02 | 0.159 | 0.203 | 0.008 | 0.051 | 20 |
| 6Star-12 | 5.0 | 39.01 | 0.418 | 0.534 | 0.006 | 0.039 | 10 |
| 6Star-129 | 5.0 | 39.01 | 0.042 | 0.054 | 0.006 | 0.039 | 10 |
| 6Star-5 | 20.0 | 156.04 | 0.170 | 0.2172 | 0.256 | 1.56 | 40 |

[†]The linear, 4-arm, and 6-arm star-shaped polymers are denoted as Lin-X, 4Star-X, and 6Star-X, respectively, wherein X indicates the DP of each arm determined for the protected t-BuA polymers.
[‡]DP not determined.

Provided in Table 2 are characterization data of the resulting polymers.

TABLE 2

Characterization of the tBu PAA homopolymers

| Polymer | [CTA]/ [monomer] ($\times 10^2$) | $DP_{arm}$ (NMR) | $M_n$ (NMR) | $M_n$ (GPC) | $M_w$ (GPC) | $M_w/M_n$ |
|---|---|---|---|---|---|---|
| Lin-27 | 4.45 | 27 | 3500 | 2100 | 4500 | 2.10 |
| Lin-151 | 0.64 | 151 | 19400 | 17700 | 34900 | 1.97 |
| Lin-323 | 0.26 | 323 | 41500 | 38400 | 82500 | 2.15 |
| Lin | 0.69 | n.d. | n.d. | 83900 | 184800 | 2.20 |
| Lin-211 | 0.69 | 211 | 27200 | 22500 | 45800 | 2.03 |
| Lin-16 | 0.13 | 16 | 2200 | 2300 | 4900 | 2.13 |
| Lin-37 | 0.52 | 37 | 4900 | 5200 | 10400 | 2.03 |
| Lin-132 | 6.67 | 132 | 17100 | 21600 | 54800 | 2.53 |
| 4Star-5 | 3.98 | 5 | 4000 | 3400 | 4000 | 1.19 |
| 4Star-8 | 2.46 | 8 | 7000 | 4800 | 6300 | 1.31 |
| 4Star-11 | 1.78 | 11 | 9200 | 5700 | 8500 | 1.49 |
| 4Star-13 | 1.46 | 13 | 10000 | n.d. | n.d. | n.d. |
| 4Star-16 | 1.20 | 16 | 13000 | n.d. | n.d. | n.d. |
| 4Star-21 | 1.38 | 21 | 11000 | n.d. | n.d. | n.d. |
| 4Star-4 | 6.36 | 4 | 3000 | 2200 | 2600 | 1.16 |
| 4Star-39 | 0.82 | 39 | 20000 | 11900 | 25600 | 2.15 |
| 4Star-130 | 0.32 | 130 | 67100 | 27200 | 72800 | 2.68 |
| 4Star-18 | 1.35 | 18 | 9800 | 7300 | 13100 | 1.80 |
| 4Star-165 | 0.13 | 165 | 85300 | 55900 | 111400 | 2.00 |
| 4Star-196 | 0.13 | 196 | 101000 | 49000 | 126400 | 2.57 |
| 6Star-3 | 5.79 | 3 | 3000 | n.d. | n.d. | n.d. |
| 6Star-21 | 0.67 | 21 | 1700 | n.d. | n.d. | n.d. |
| 6Star-24 | 0.26 | 24 | 19000 | 40800 | 88500 | 2.17 |
| 6Star-12 | 1.37 | 12 | 10000 | 7300 | 11800 | 1.62 |
| 6Star-129 | 0.14 | 129 | 100000 | 53900 | 115100 | 2.13 |
| 6Star-129 | 0.14 | 129 | 100000 | 47200 | 118400 | 2.51 |
| 6Star-238 | 0.69 | 238 | 184000 | 79800 | 182500 | 2.29 |
| 6Star-253 | 0.69 | 253 | 195500 | 80400 | 170200 | 2.12 |

As shown in Table 2, as the ratio of CTA to monomers was increased, the molecular weight (measured by GPC and NMR) of polymers decreased, giving a series of star-shaped and comparative linear polymers with Mn and Mw of about 2,000 to about 200,000 g/mol.

To probe the chain transfer polymerization, the relationship between the ratio of the thiol groups (which were present for chain transfer in the exemplified chain transfer agents, although other moieties could alternatively be used) to monomers and the polymer chain length was examined. The Mayo plots (1/DP or 1/Mn vs. [SH]/[monomer]) for the comparative linear polymers, as well as the 4-arm, and 6-arm star-shaped polymers showed linear correlations based on eq. (1) (FIG. 1), and the $C_{tr}$ value (i.e., the chain transfer constant) of each CTA was determined as the slope of fitted lines in the Mayo plots ($C_{tr}$=0.91 (Lin), 1.06 (4Star), 0.97, (6Star)).

$$\frac{1}{DP_{arm}} = \frac{1}{DP_0} + C_{tr} \frac{[SH]}{[Monomer]} \quad (1)$$

In addition, the plots of 1/Mn (determined by GPC) against [SH]/[Monomer] (i.e. [the number of thiol groups in a CTA]×[CTA]/[M]) also showed linear correlations (FIG. 1). These results demonstrate that the polymerization was driven by an independent chain transfer process initiated by each thiol group of the CTAs, thus supporting the formation of star-shaped polymers. These results further suggested that a polymer chain grew from each CTA arm, and the average polymer chain arm length could be controlled by varying the ratio of CTA to monomers.

Synthesis of Tert-Butyl Poly(Acrylic Acid)/Methacrylate (t-Bu PAA/MA) Copolymers Random t-Bu PAA copolymers with methacrylate (MA), were synthesized using the same method as Example 1, under the conditions provided in Table 3, below. CTA (i.e., PETMP) was used in an amount of 0.098 g (0.2 mmol), AIBN was used in an amount of 1.56 mmol, and acetonitrile was used in an amount of 40 g. The ratio of CTA to monomer was 0.001.

TABLE 3

Polymerization conditions for tBu PAA/MA copolymers

| Polymer[†] | t-BuA (g) | t-BuA (mmol) | MA (g) | MA (mmol) | MA % (mol. %) | MA (mol. %) protected | MA (mol. %) deprotected |
|---|---|---|---|---|---|---|---|
| 4StarMA$_{20}$-171 | 16.0 | 124.8 | 2.69 | 31.2 | 20 | 19 | 20 |
| 4StarMA$_{34}$-208 | 12.0 | 93.6 | 5.37 | 62.4 | 40 | 37 | 34 |
| 4StarMA$_{56}$-171 | 8.0 | 62.4 | 8.06 | 93.6 | 60 | 56 | 56 |

[†]The 4-arm star-shaped polymers are denoted as 4Star$_y$-X, wherein X indicates the DP of each arm, and y indicates the mole percentage of MA in the polymer.

As shown in Table 3, the mole percentages of methyacrylate in the polymers were close to the initial feed ratios, indicating that the MA monomers were quantitatively incorporated to the polymer chains.

TABLE 4

Characterization of the tBu PAA/MA copolymers

| Polymer | MA (mol. %) | DP (NMR) | $M_n$ (NMR) | $M_n$ (GPC) | $M_w$ (GPC) | $M_w/M_n$ |
|---|---|---|---|---|---|---|
| 4StarMA$_{20}$-208 | 20 | 208 | 100700 | 61588 | 128174 | 2.08 |
| 4StarMA$_{34}$-171 | 34 | 171 | 77500 | 49368 | 102699 | 2.08 |
| 4StarMA$_{56}$-215 | 56 | 215 | 90300 | 30443 | 75959 | 2.49 |

Therefore, Example 1 demonstrates the synthesis of star-shaped polymers according to the disclosure.

Example 2: HAP Binding Assay

The binding behavior of rhodamine-labeled polymers to hydroxyapatite (HAP) (as a model for a tooth enamel surface) was explored. Rhodamine B-labeled copolymers were synthesized using methacryloxyethyl thiocarbamoyl rhodamine B (0.1 mol. % to the total amount of monomers) by the same method as Example 1, under the conditions provided in Table 5, below. For the comparative linear polymers, 0.156 mmol (0.0256 g) of AIBN was used. For the star-shaped polymers, 0.078 mmol (0.013 g) of AIBN was used. The components were mixed in a 2:1 acetonitrile:DMF solution.

TABLE 5

Polymerization conditions for rhodamine B-labeled polymers

| Polymer | t-BuA (g) | t-BuA (mmol) | CTA (g) | CTA (mmol) | [CTA]/[M] |
|---|---|---|---|---|---|
| F-Lin-16 | 2.0 | 15.6 | 0.125 | 1.040 | 0.067 |
| F-Lin-50 | 2.0 | 15.6 | 0.037 | 0.312 | 0.020 |
| F-Lin-134 | 2.0 | 15.6 | 0.0125 | 0.104 | 0.007 |
| F-Lin-189 | 1.0 | 7.802 | 0.005 | 0.040 | 0.005 |
| F-4Star-19 | 1.0 | 7.802 | 0.051 | 0.105 | 0.013 |
| F-4Star-47 | 1.0 | 7.802 | 0.019 | 0.039 | 0.005 |
| F-4Star-87 | 1.0 | 7.802 | 0.0095 | 0.0195 | 0.003 |
| F-4Star-124 | 1.0 | 7.802 | 0.006 | 0.013 | 0.002 |
| F-4Star-192 | 1.0 | 7.802 | 0.005 | 0.010 | 0.001 |
| F-6Star-12 | 1.0 | 7.802 | 0.085 | 0.109 | 0.014 |
| F-6Star-121 | 1.0 | 7.802 | 0.008 | 0.011 | 0.001 |

The polymer solutions with different concentrations (pH 7, adjusted by NaOH aq., 0.5 mL, 0.04, 0.08, 0.16, 0.31, 0.63, and 1.25 g/L) were incubated with HAP (30 mg/mL) in a 1.5 ml tube in a buffer solution. The solution was gently shaken using a mechanical shaker for 2 h at room temperature and then centrifuged at 10,000 rpm for 10 min. The fluorescence emission intensities of the supernatant were measured (excitation wavelength=553 nm, emission wavelength=627 nm) and compared with those for samples with same concentration of polymers without HAP to calculate the amount of polymers that remained free in supernatant at equilibrium ($C_{eq}$), and the amount of polymers that adsorbed onto the HAP surface (q). The amount of polymers adsorbed onto the HAP surface increased as the polymer concentration was increased and appeared to level off at high concentrations. The adsorption isotherms were represented by Equation 2 for the Langmuir adsorption model:

$$q = \frac{q_{max} C_{eq}}{K_d + C_{eq}} \qquad (2)$$

or its linear form, as represented by Equation 3:

$$\frac{C_{eq}}{q} = \frac{K_d}{q_{max}} + \frac{C_{eq}}{q_{max}} \qquad (3)$$

where $q_{max}$ and $K_d$ are the maximum amount of adsorbed polymers and the dissociation constant, respectively.

The data were linear and fitted by Eq. 2 well, except the data points at the highest polymer concentrations. Without intending to be bound by theory, this may have been due to polymer aggregation in solution, which has been reported to occur for the adsorption of acrylate polymers on HAP. The $q_{max}$ and $K_d$ values were calculated from these data, and are shown in Table 6, below, along with other polymer characterization data. The number average molecular weight ($M_n$) of the deprotected acrylic polymers, which could not be measured by NMR, was estimated based on the DP of the protected tBu polymers and the molecular weights of the CTA and acrylic acid.

TABLE 6

Polymer characterization and HAP binding

| Polymer | DP$_{arm}$ (NMR) | $M_n$ | Max. adsorption, $q_{max}$ (mg/HAP g) | (μmol/HAP g) | $K_d$ (mg/mL) | (μmol/L) |
|---|---|---|---|---|---|---|
| F-Lin-16 | 16 | 1300 | 3.9 ± 0.5 | 3.04 ± 0.42 | 69 ± 18 | 53.2 ± 13.7 |
| F-Lin-50 | 50 | 3800 | 9.2 ± 1.0 | 2.44 ± 0.27 | 171 ± 8 | 45.3 ± 2.1 |
| F-Lin-134 | 134 | 9840 | 10.3 ± 1.4 | 1.05 ± 0.14 | 66 ± 35 | 6.7 ± 3.6 |
| F-Lin-189 | 189 | 13800 | 14.5 ± 2.0 | 1.05 ± 0.14 | 205 ± 76 | 14.8 ± 5.5 |
| F-4Star-19 | 19 | 5900 | 13.7 ± 1.6 | 2.34 ± 0.27 | 164 ± 63 | 27.8 ± 10.7 |
| F-4Star-47 | 47 | 14000 | 11.1 ± 2.1 | 0.79 ± 0.15 | 30 ± 17 | 2.1 ± 1.2 |
| F-4Star-87 | 87 | 26000 | 9.7 ± 0.9 | 0.38 ± 0.03 | 55 ± 37 | 2.2 ± 1.5 |
| F-4Star-124 | 124 | 36200 | 10.0 ± 0.9 | 0.28 ± 0.02 | 38 ± 27 | 1.1 ± 0.7 |
| F-4Star-192 | 192 | 55800 | 18.5 ± 3.1 | 0.33 ± 0.06 | 76 ± 24 | 1.4 ± 0.4 |
| F-6Star-12 | 12 | 6100 | 10.7 ± 2.3 | 1.76 ± 0.38 | 72 ± 30 | 11.9 ± 5.0 |
| F-6Star-121 | 121 | 5320 | 20.0 ± 3.7 | 0.38 ± 0.07 | 114 ± 33 | 2.1 ± 0.6 |

TABLE 6-continued

Polymer characterization and HAP binding

| Polymer | $DP_{arm}$ (NMR) | $M_n$ | Max. adsorption, $q_{max}$ (mg/HAP g) | Max. adsorption, $q_{max}$ (μmol/HAP g) | $K_d$ (mg/mL) | $K_d$ (μmol/L) |
|---|---|---|---|---|---|---|
| F-4StarMA$_{18}$-131 | 131 | 39500 | 16.5 ± 2.3 | 0.42 ± 0.06 | 115 ± 42 | 2.9 ± 1.1 |
| F-4StarMA$_{37}$-185 | 185 | 57700 | 18.8 ± 1.9 | 0.33 ± 0.03 | 263 ± 49 | 4.6 ± 0.8 |
| F-4StarMA$_{55}$-149 | 149 | 48100 | 13.3 ± 0.8 | 0.28 + 0.02 | 75 ± 31 | 1.6 ± 0.6 |

Figure 2:
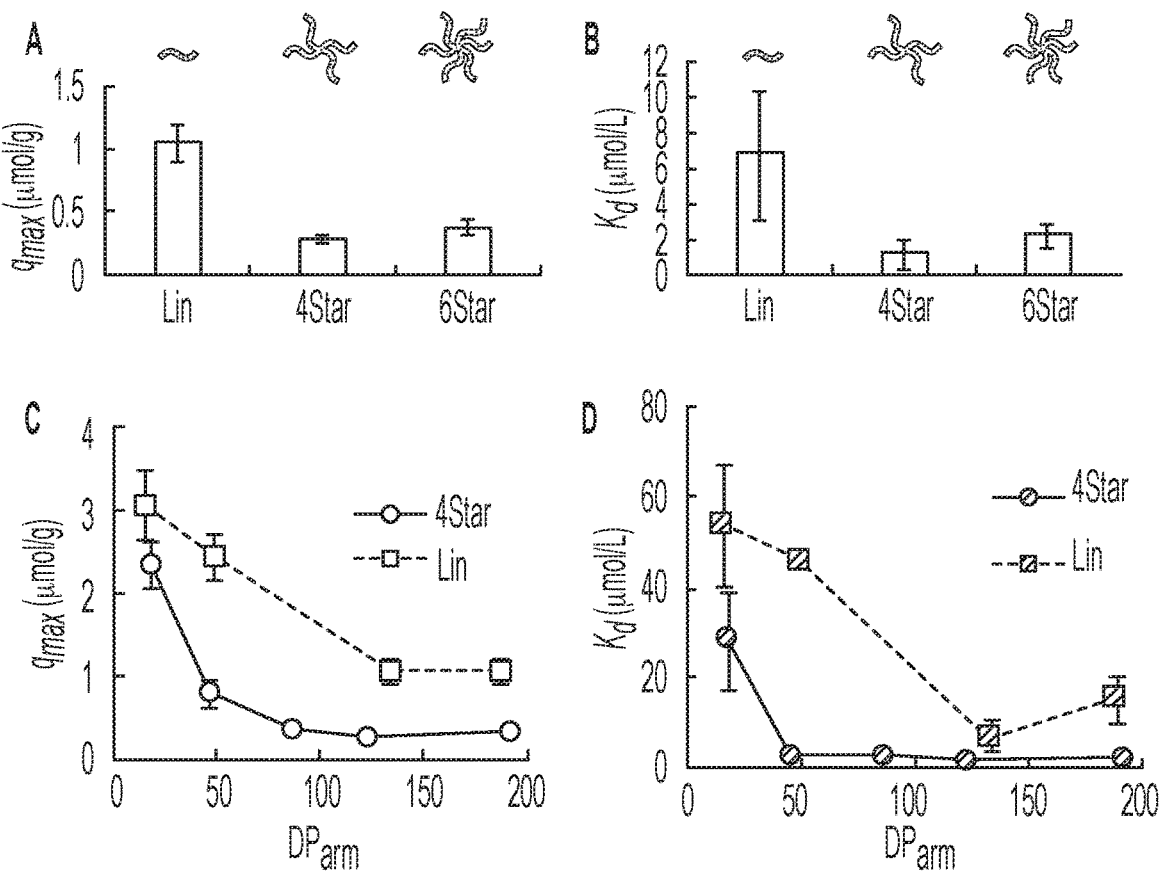
FIG. 2A illustrates the maximum adsorption ($q_{max}$) of the star-shaped polymers of the disclosure to a HAP surface.
FIG. 2B illustrates the dissociation constant ($K_d$) of the star-shaped polymers of the disclosure to a HAP surface.
FIG. 2C illustrates the impact of the polymer arm length (DP) on the adsorption ($q_{max}$) of the star-shaped polymer to a HAP surface.
FIG. 2D illustrates the impact of the polymer arm length (DP) on the dissociation constant ($K_d$) of the star-shaped polymer to a HAP surface.

As shown in Table 6 and in FIG. 2A, the $q_{max}$ values (i.e. adsorption to HAP surface) for 4- and 6-arm star-shaped polymers were lower than that of the comparative linear polymers. Without intending to be bound by theory, this was likely due to the larger molecular sizes of star-shaped polymers, which occupy larger areas on the hydroxyapatite surface than the comparative linear polymer, so that fewer star-shaped polymers could be bound to the hydroxyapatite surface. In contrast, however, the dissociation constant, $K_d$, values of star-shaped polymers were significantly smaller than that of the comparative linear polymer (FIG. 2B), indicating that the star-shaped polymers adsorbed on the hydroxyapatite surface more strongly than the comparative linear polymer. Without intending to be bound by theory, it is believed this is due to the larger polymer sizes of star-shaped polymers which have more contact points on the hydroxyapatite surface for binding. The 4- and 6-arm star-shaped polymers showed the similar $q_{max}$ and $K_d$, indicating that these polymers occupy similar areas on the HAP surfaces and have similar binding affinity.

The $q_{max}$ and $K_d$ values of the 4-star and comparative linear polymers appeared to decrease and level off at large DPs (FIGS. 2C, 2D). These results suggest that the maximum number of adhered polymers and their binding affinity did not increase once the size of polymers became sufficiently large. Without intending to be bound by theory, it is believed that this leveling-off of HAP binding behavior of the polymers occurs due to the anionic carboxylic groups of the polymer side chains binding ligand to HAP surfaces through electrostatic interactions. Therefore, as the polymer chains becomes longer, having more carboxylic side chains, the binding affinity of polymers for HAP increases. However, the binding of carboxylic side chains to HAP surfaces requires the polymer chains to be flattened and/or stretched on the HAP surface, which is not favorable due to large entropic penalty. Therefore, the binding of polymers is determined by the balance between the two driving forces to maximize the number of binding sites by carboxylic groups on the HAP surface (enthalpy gain) and minimize the strain on polymer chains (entropic penalty). As the DP of polymers increases, the number of carboxylic side chain groups increases, thus increasing their binding. However, once the polymers are long enough, it becomes difficult to constrain the polymer chains on the HAP surface due to entropic penalty, resulting in the leveling of $q_{max}$ and $K_d$.

Figure 3:
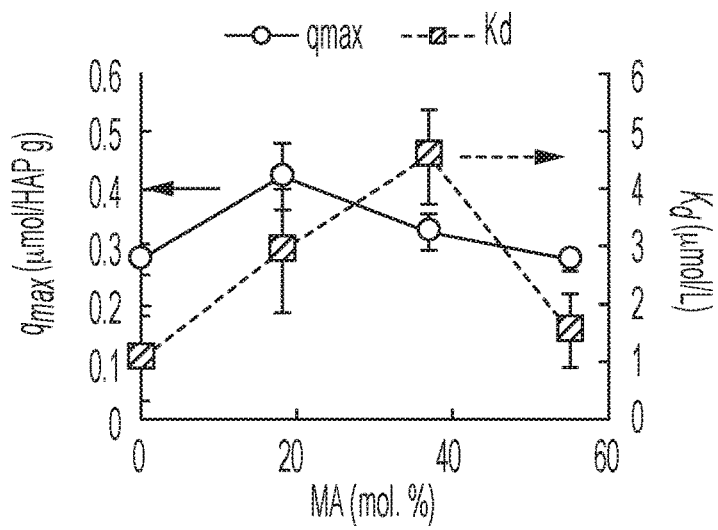
FIG. 3 illustrates the effect of hydrophobic monomer composition on HAP adsorption of a 4-arm star-shaped polymer according to the disclosure.

Furthermore, the random copolymers with hydrophobic monomer MA (which is relatively more hydrophobic than acrylates, even alkylated acrylates such as t-butyl acrylate) showed variation in binding as the composition of MA was increased (FIG. 3). Without intending to be bound by theory, this binding behavior may be explained by the interplay between the electrostatic binding of carboxylate groups to HAP and the intramolecular and intermolecular associations of MA groups. Increasing the MA composition reduces the number of carboxylic side chains, which may in turn reduce the binding affinity of polymers to HAP (higher $K_d$). On the other hand, the hydrophobic groups may associate intramolecularly (within the same star-shaped polymer), which may prevent the extension of polymer chains for binding, also resulting in low binding affinity (higher $K_d$). Therefore, the increase in the $K_d$ values for the low percentage of MA may indicate that the intramolecular association and/or reduced number of acidic groups are dominant. However, high affinity (low $K_d$) value for the polymer with 55% MA indicates the intermolecular hydrophobic association between star-shaped polymers may play an important role to stabilize the polymer layer. On the other hand, the $q_{max}$ also slightly increased, indicating the conformation of bound polymer chains are more compact (smaller occupied surface area). The polymers with 55% MA showed lower $q_{max}$, indicating the polymer chains are more expanded likely due to increased intermolecular associations of MA groups between star-shaped polymers, which is in good agreement with the low $K_d$ value. These results demonstrate that the binding behaviors of polymers to HAP surfaces can be controlled by their hydrophobicity.

Example 2 demonstrates that the star-shaped polymers of the disclosure can bind to HAP surfaces and have higher binding affinity as compared to comparative linear polymers. Example 2 further demonstrates that the hydrophobic interactions due to methacrylate monomers can help stabilize the polymer on the HAP surface.

Example 3: Anti-Bacterial Adhesion Assay

Various comparative linear and star-shaped polymers having DPs ranging from 100 to 200 and varying degrees of hydrophobicity were selected to examine the effect of the composition and shape of the polymers on anti-bacterial attachment activity.

HAP coated MBEC™ lids were treated by polymer solutions (1 wt %, pH 6.5 adjusted with NaOH or HCl) and allowed to shake in the incubator at 37° C. for 1 h. Following treatment, excess polymer solution was removed from the MBEC™ lids by submerging in Trypticase Soy Broth (TSB) for 10-15 sec for three cycles, replacing the TSB broth for each new cycle. Both untreated and polymer-treated MBEC™ lids were then incubated with freshly prepared overnight cultures of mixed *Actinomyces viscosus* (ATCC #43146) and *Streptococcus oralis* (ATCC #35037) for 3 h at 37° C. After incubation the MBEC™ lids were submerged in TSB and sonicated two times for 2 min each time in order to detach the HAP bound bacteria into the TSB. The BacTiter-Glo Microbial Cell Viability Assay was utilized on the re-suspended TSB to determine the percent reduction. The percent reduction was calculated by the following equation: % reduction=100×(bacteria attached on untreated surface−bacteria attached on polymer-treated surface)/bacteria on untreated surface. One-way analysis of variance (ANOVA) was used to assess the treatment effect. A Tukey multiple comparison test was used to assess pairwise treatment differences. A p<0.05 was used to indicate significant statistical differences.

Figure 4:
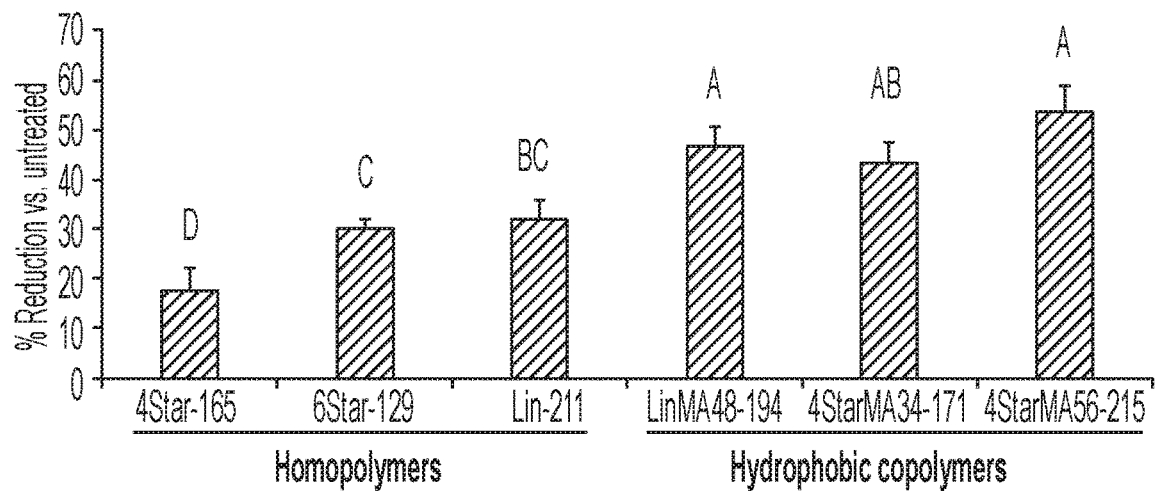
FIG. 4 illustrates the anti-bacterial attachment activity of the star-shaped polymers according to the disclosure.

As shown in FIG. 4, all the polymers reduced attachment of the oral bacteria to the HAP surface by 17-54%, relative to an untreated control. The hydrophobic random comparative linear copolymers (LinMA48-194) and 4-arm star-shaped copolymers (4StarMA34-171 and 4StarMA56-215) showed higher percent reductions (43-54%) in bacterial attachment as compared to both comparative linear and star-shaped homopolymers, suggesting that the hydrophobic monomer groups improve the ability of polymers to reduce bacterial attachment.

Accordingly, Example 3 further demonstrates that the incorporation of hydrophobic groups into the star-shaped polymer of the disclosure results in improved reduction in bacterial attachment to HAP surfaces, as compared to relatively more hydrophilic star-polymers.

As shown by Examples 2 and 3, these data further suggest that, while the hydrophobicity of the polymers resulted in an enhanced effect of anti-bacterial adhesion, the enhanced effect was not due to the difference in the inherent binding properties of the polymers to HAP surfaces, but rather related to the physicochemical properties of the polymers or the conformations of the polymers on the surface of the HAP.

The ability for a polymer to provide anti-bacterial attachment effects to an oral surface can only happen if the polymer can sufficiently bind to the oral surface (e.g., the copolymer has a $K_d$ of less than about 5 µmol/L). A multi-arm star-shaped polymer had significantly better binding to HAP. Similarly, hydrophobicity of the polymer significantly decreased bacteria attachment, even though it did not significantly affect the $K_d$. Therefore, the data of Examples 2 and 3 suggest that a hydrophobic star-shaped polymer would provide the most effective oral composition, because such a star-shaped polymer demonstrates significantly improved binding to HAP as well as improved anti-bacterial properties.

Example 4: Contact Angle Measurements

Contact angle was performed on an Attension Theta instrument from Biolin Scientific. Data was analyzed using One Attension software v 2.9. Briefly, 1.0 wt % polymer solutions were prepared, and their pH adjusted to 6.5 with concentrated NaOH or HCl. Due to the immediate absorption of solution droplets into hydroxyapatite, surface modification was required prior to treatment with polymer solutions in order to obtain stable droplets for comparison. Sintered HAP was first treated with modified artificial saliva[47] for 1 hour (see Supporting Information). After this time, the discs were soaked in 2 mL of polymer solution for three hours on an orbital shaker. The discs were removed and rinsed slightly to remove excess or loosely bound material, and then dried overnight. Contact angle measurements were collected and averaged using four separate measurements of a 3 µL droplet.

Figure 5:
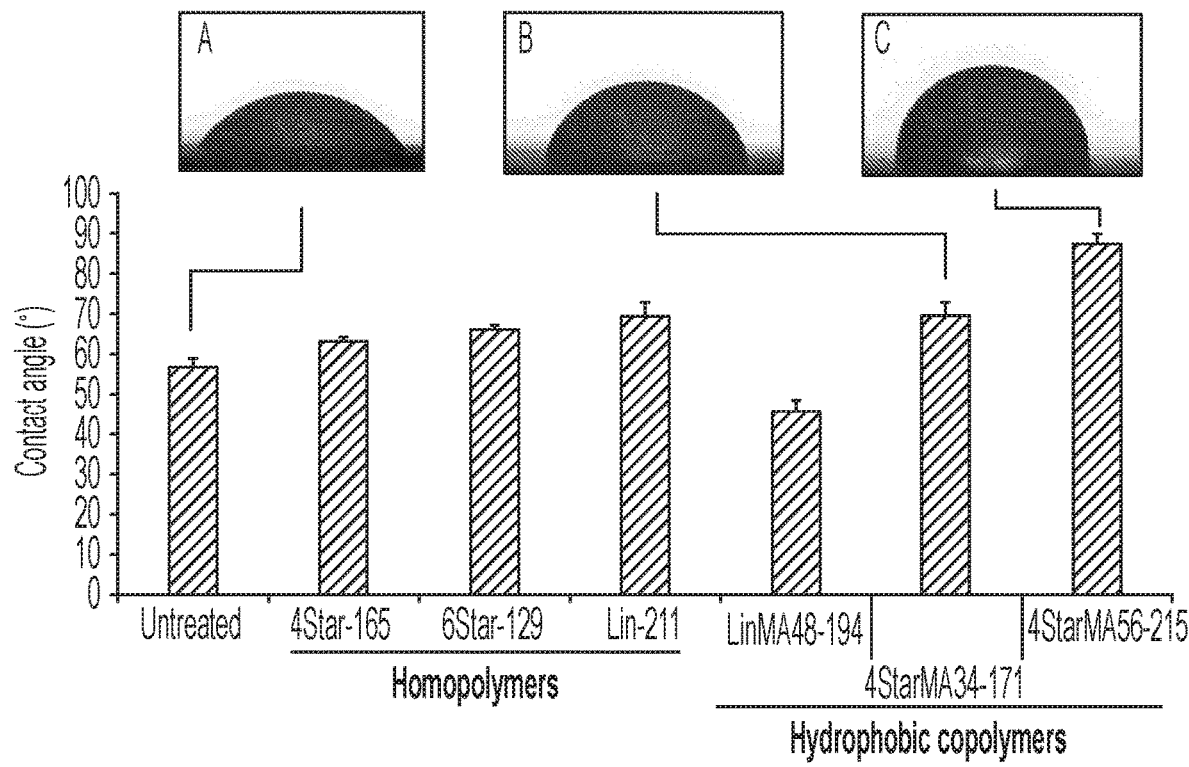
FIG. 5 illustrates the effect on contact angle of the star-shaped polymers according to the disclosure.

As shown in FIG. 5, an increase in contact angle of greater than 7° was observed for most polymer samples, indicating that most of the polymer-treated surfaces were more hydrophobic than the untreated control. The magnitude of this difference also reflected the compositional changes within the polymers themselves. 4StarMA$_{56}$-171, for example, had the highest contact angle of 87.6°, an effect attributed to the 56% MA concentration within the polymer.

Example 4 illustrates that the star-shaped polymers of the disclosure are effective at modulating the properties and functions of HAP surfaces, even in the presence of a protein layer, which can lead to the prevention of attachment of oral bacteria.

The results of the foregoing examples suggest that the surface attachment may be more dependent on polymer shape (e.g., linear vs. star-shaped), while the anti-bacterial attachment, may be more dependent on the composition of the polymer (e.g., hydrophobicity).

What is claimed is:

1. An oral care composition comprising a star-shaped polymer and an orally acceptable carrier, wherein the star-shaped polymer has a structure according to Formula (I):

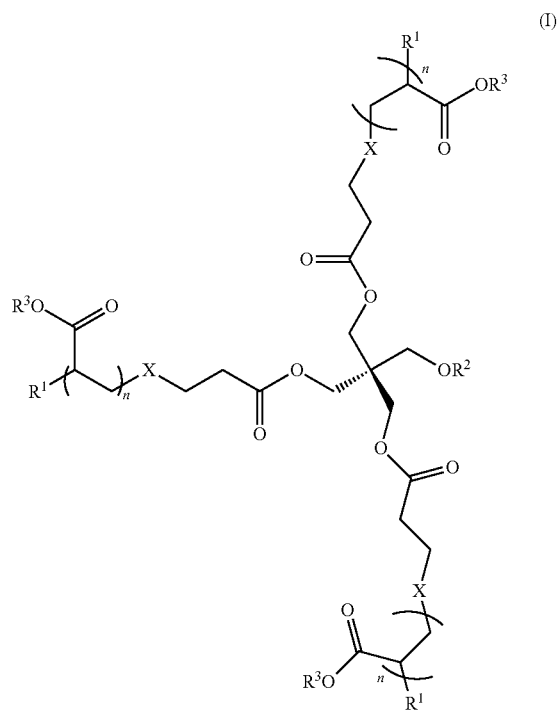

wherein:
each $R^1$ independently comprises H or an acrylate polymer,
each n independently is 5 to 500,
each X is independently O, $NR^4$, or S, wherein $R^4$ comprises H or $C_{1-6}$alkyl,
$R^2$ comprises H, $C_{1-8}$alkyl, or a functionalized acrylate polymer, and
each $R^3$ independently comprises H, $C_{1-8}$alkyl, or $C_{1-8}$alkyl phosphate.

2. The oral care composition according to claim 1, wherein X is O.

3. The oral care composition according to claim 1, wherein X is S.

4. The oral care composition according to claim 1, wherein $R^1$ is an acrylate polymer selected from the group consisting of polymethacrylate, poly(ethyl acrylate), poly(propyl acrylate), poly(butyl acrylate), and poly($C_{1-8}$alkyl phosphate acrylate).

5. The oral care composition according to claim 1, wherein $R^2$ is a functionalized acrylate co-polymer having a structure according to one of the following Formulae:

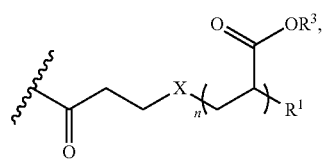
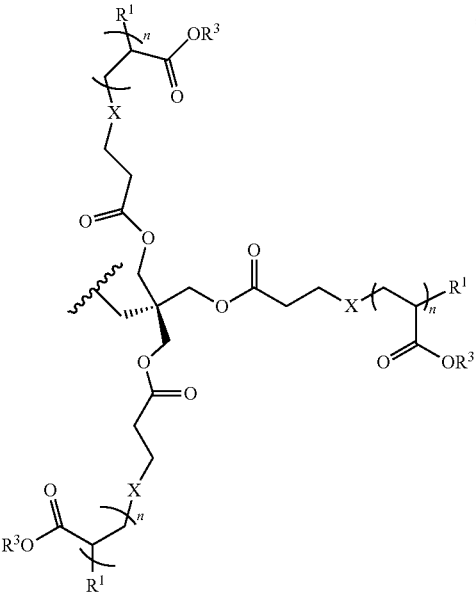
(IA)
(IB)
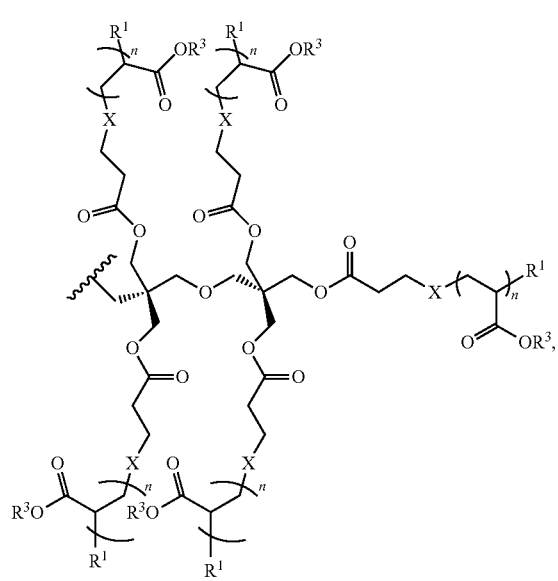
(IC)

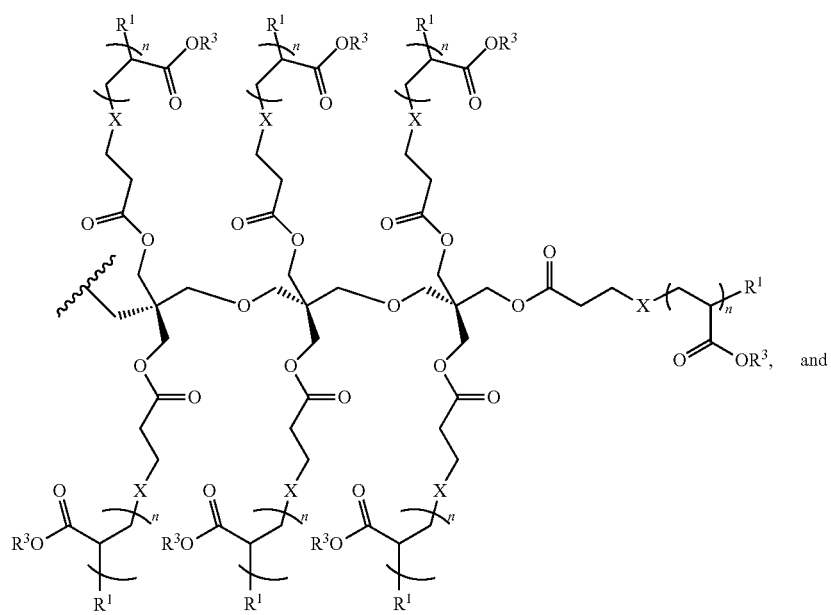

(ID)

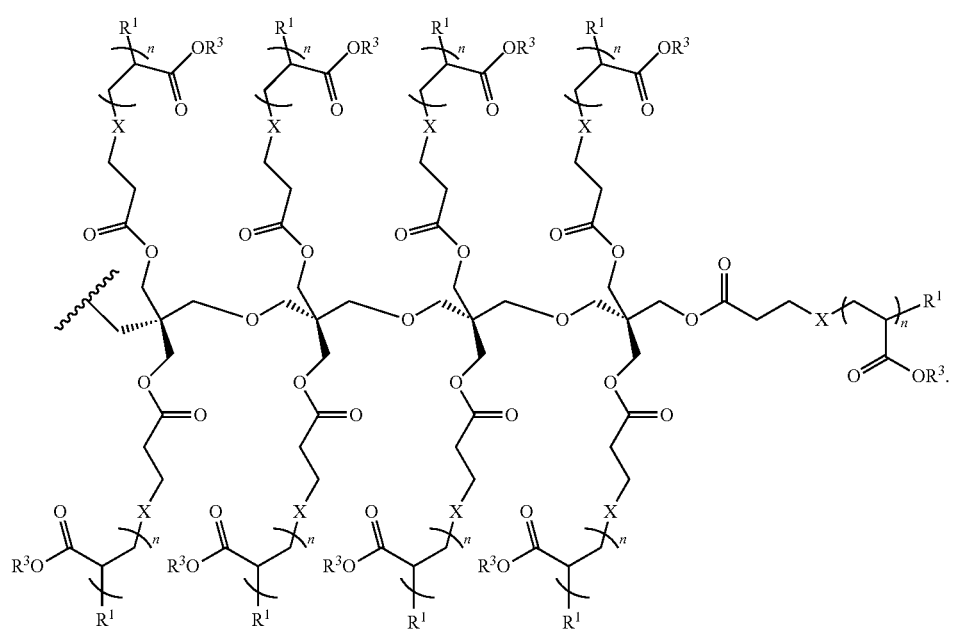

(IE)

6. The oral care composition according to claim 1, wherein the number average molecular weight of the star-shaped polymer is about 1,000 to about 700,000 grams per mole.

7. The oral care composition according to claim 1, wherein the weight average molecular weight of the star-shaped polymer ranges from about 10,000 to about 150,000 g/mol.

8. The oral care composition according to claim 1, wherein the mole percentage of methacrylate repeat units in the star-shaped polymer ranges from about 5 to about 70 mol. %.

9. The oral care composition according to claim 1, wherein the composition comprises about 0.1 weight percent (wt. %) to about 10 wt. % of the star-shaped polymer, based on the total weight of the composition.

10. The oral care composition according to claim 1, wherein the composition is a mouthwash, a toothpaste, a tooth gel, a tooth powder, a non-abrasive gel, a mousse, a foam, a mouth spray, a lozenge, an oral tablet, a dental implement, or a pet care product.

11. The oral care composition according to claim 1, wherein the orally acceptable carrier comprises water, a thickener, a buffer, a humectant, a surfactant, an abrasive, a sweetener, a mouth-feel agent, a flavorant, a colorant, an anti-caries agent, an anti-bacterial or antimicrobial agent, an anti-plaque agent, a cleaning agent, an adhesion agent, a foam modulator, a whitening agent, a tartar control (anti-calculus) agent, a saliva stimulating agent, an antisensitivity or desensitizing agent, an antioxidant, a nutrient, a preservative, an enzyme, or any combination thereof.

12. A star-shaped polymer having the structure according to Formula (I):

wherein:

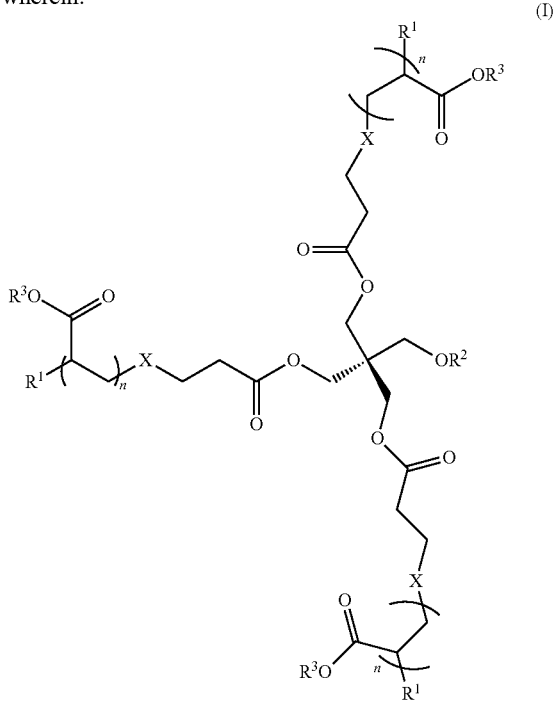

each $R^1$ independently comprises H or an acrylate polymer, each n independently is 5 to 500, each X is independently O, $NR^4$, or S, wherein $R^4$ comprises H or $C_{1-6}$alkyl, $R^2$ comprises H, $C_{1-8}$alkyl, or a functionalized acrylate polymer, and each $R^3$ independently comprises H, $C_{1-8}$alkyl, or $C_{1-8}$alkyl phosphate.

13. The star-shaped polymer according to claim 12, wherein X is O.

14. The star-shaped polymer according to claim 12, wherein X is S.

15. The star-shaped polymer according to claim 12, wherein $R^1$ is an acrylate polymer selected from the group consisting of polymethacrylate, poly(ethyl acrylate), poly(propyl acrylate), poly(butyl acrylate), and poly($C_{1-8}$alkyl phosphate acrylate).

16. The star-shaped polymer according to claim 12, wherein $R^2$ is a functionalized acrylate co-polymer having a structure according to one of the following Formulae:

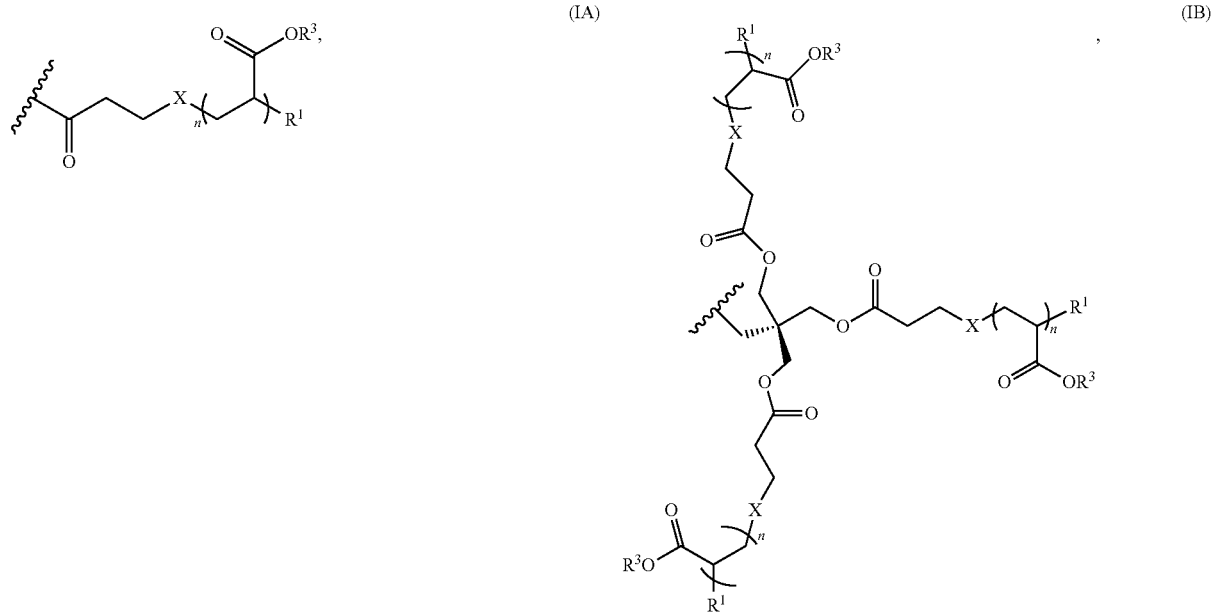

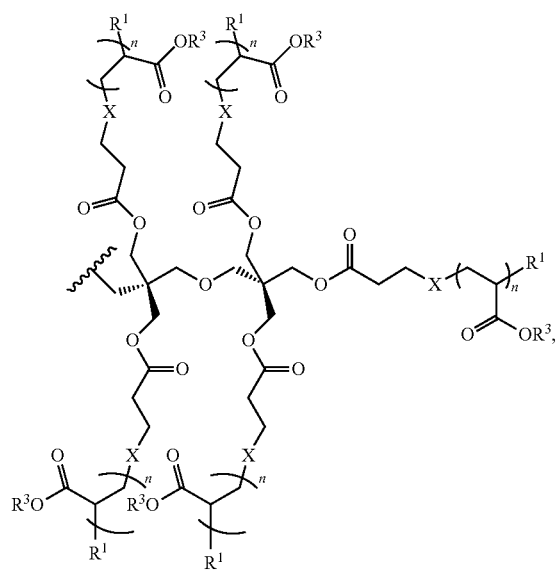
(IC)
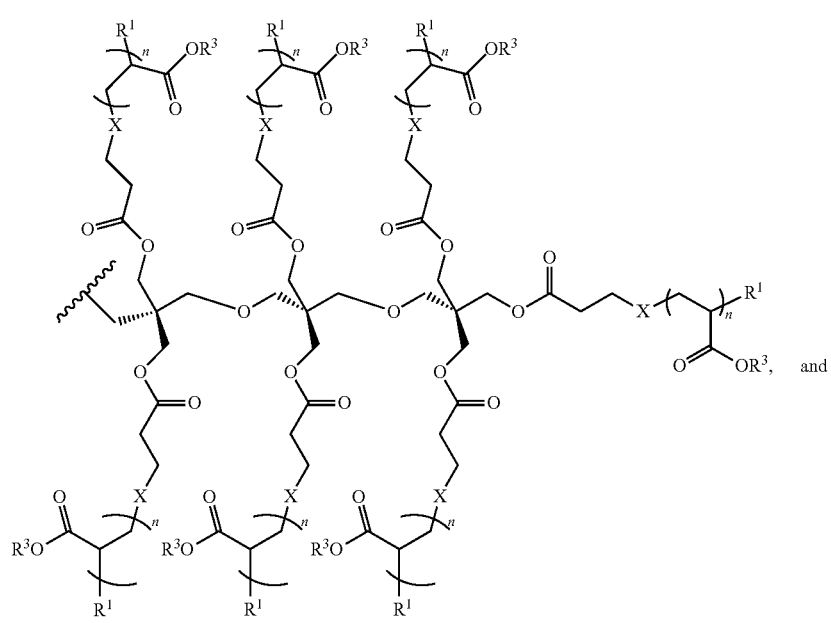
(ID) and

-continued (IE)

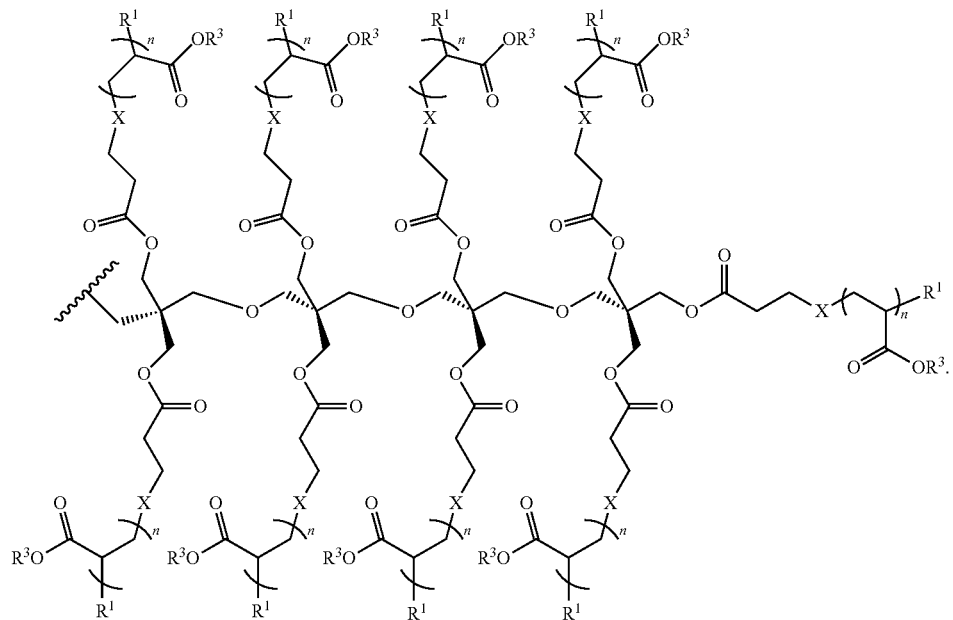

17. The star-shaped polymer according to claim 12, wherein the number average molecular weight of the star-shaped polymer is about 1,000 to about 700,000 grams per mole.

18. The star-shaped polymer according to claim 12, wherein the weight average molecular weight of the star-shaped polymer ranges from about 10,000 to about 150,000 g/mol.

19. The star-shaped polymer according to claim 12, wherein the star-shaped polymer has a content of hydrophobic monomers of at least about 5 mol %.

20. The star-shaped polymer according to claim 12, wherein the mole percentage of methacrylate repeat units in the star-shaped polymer ranges from about 5 to about 70 mol. %.

21. The star-shaped polymer according to claim 12, wherein the star-shaped polymer has a structure selected from the group consisting of:

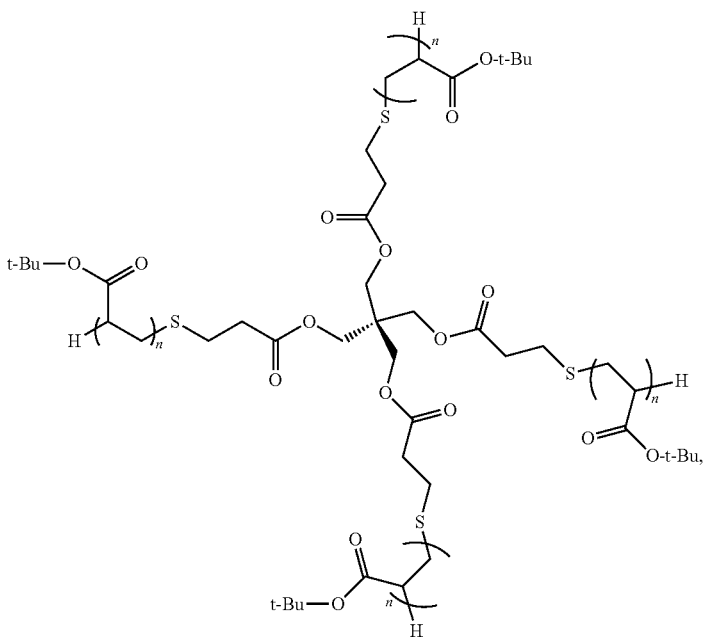

-continued
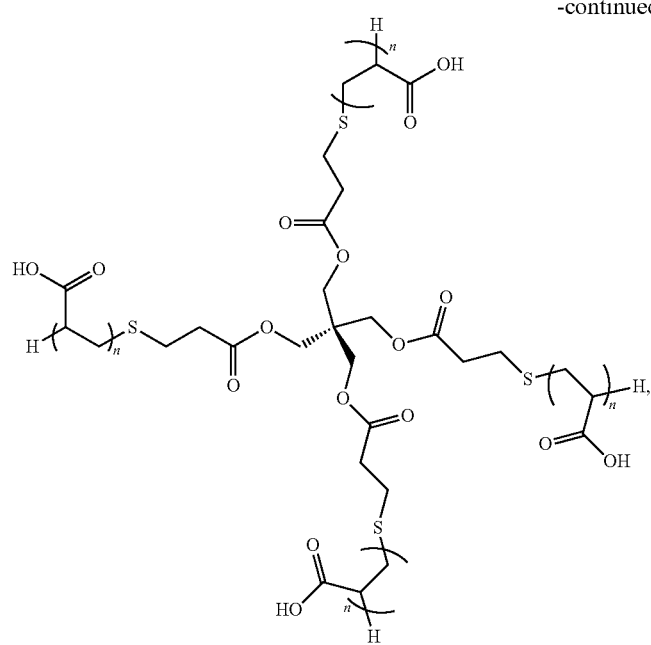
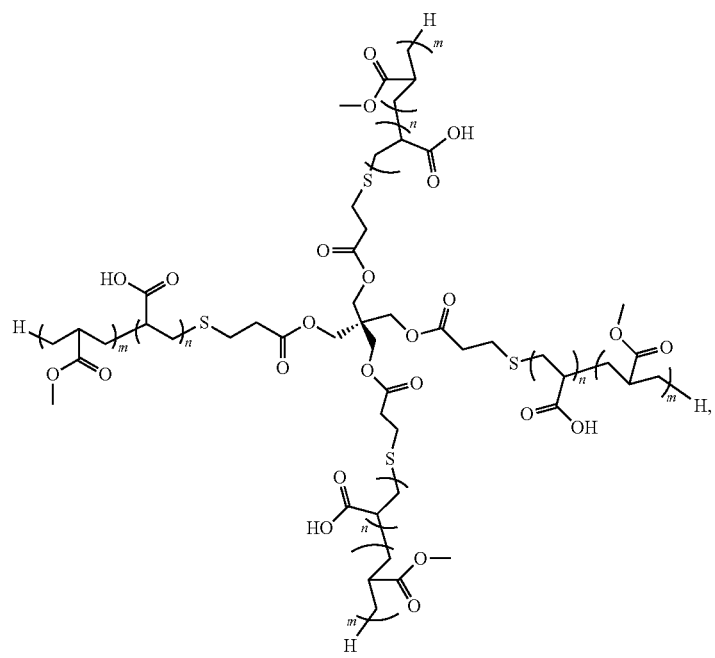

-continued
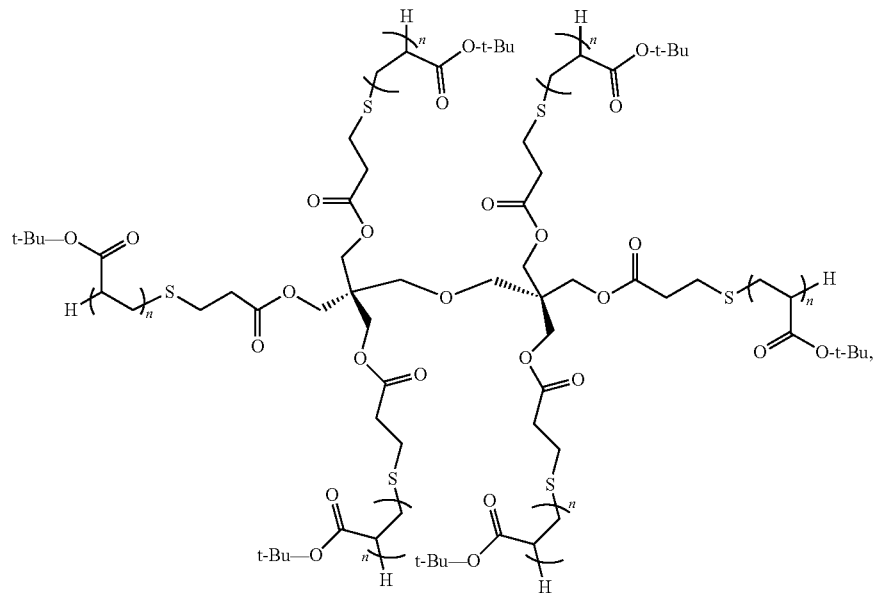
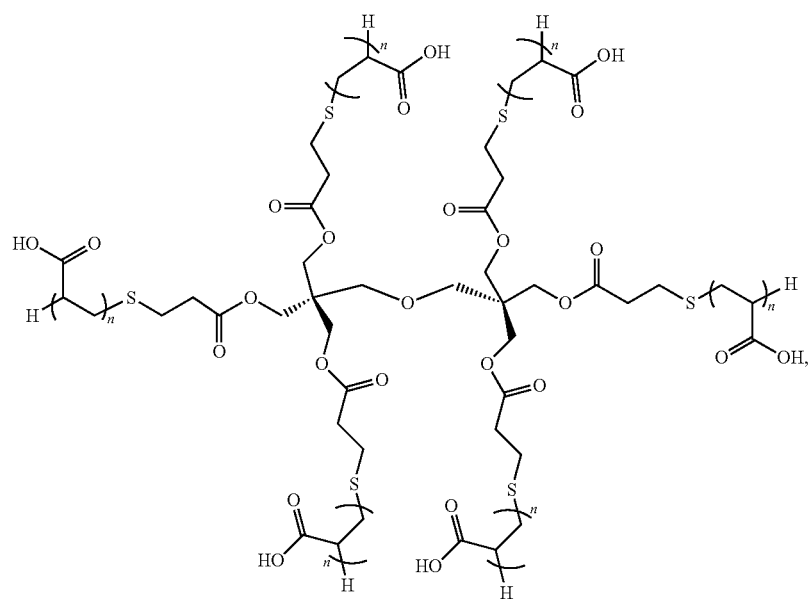

-continued
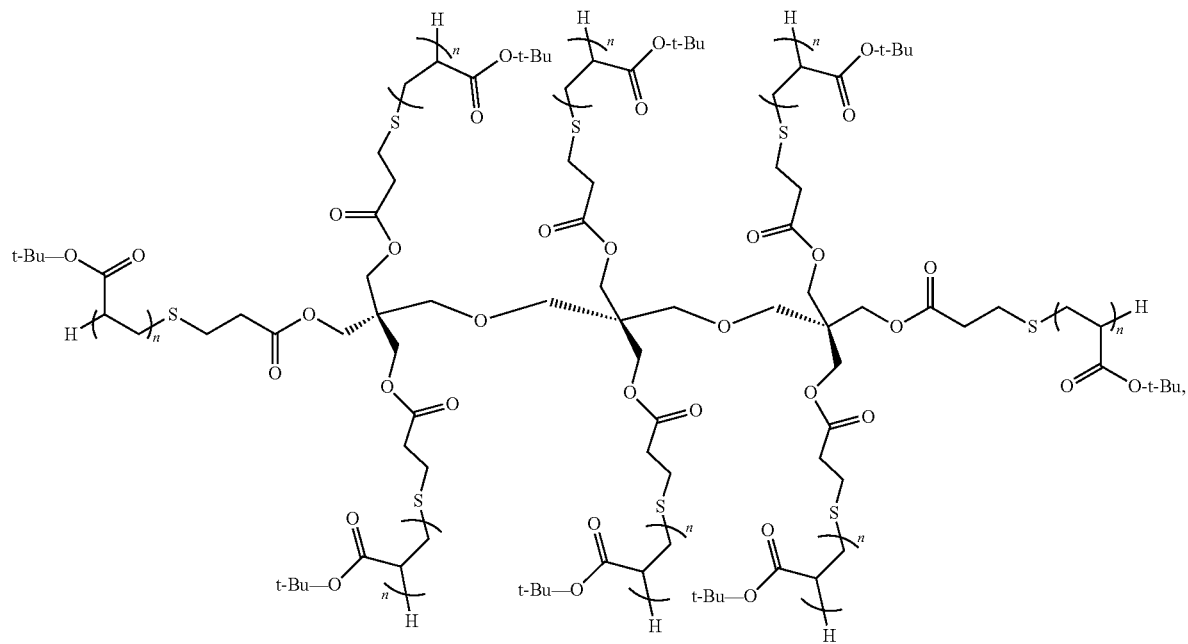
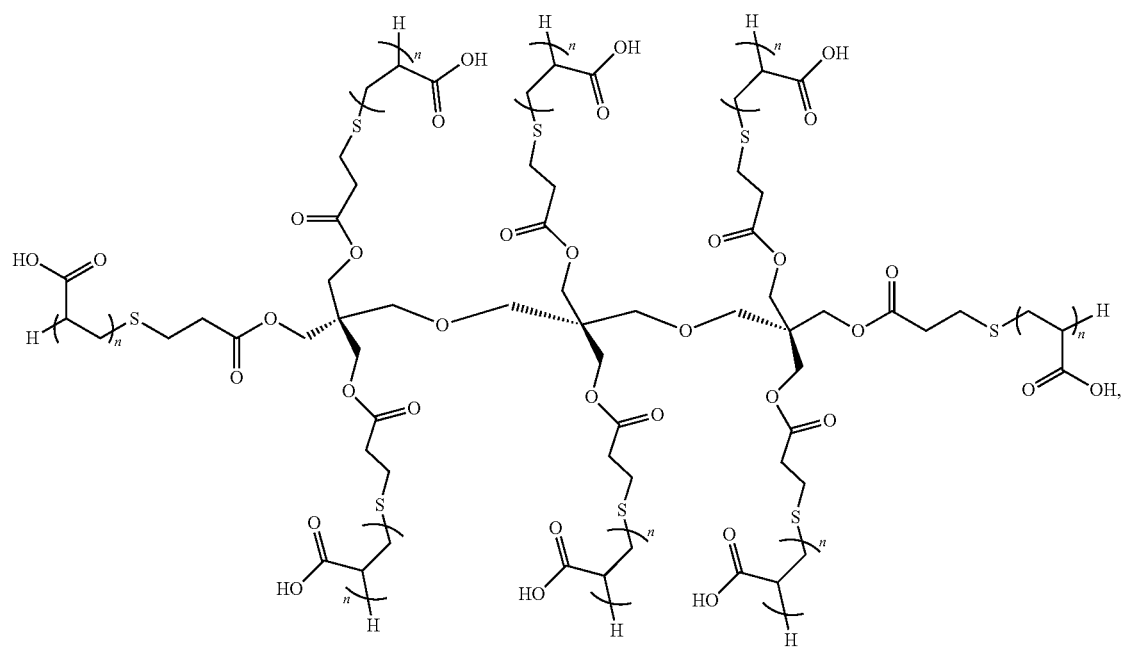

-continued
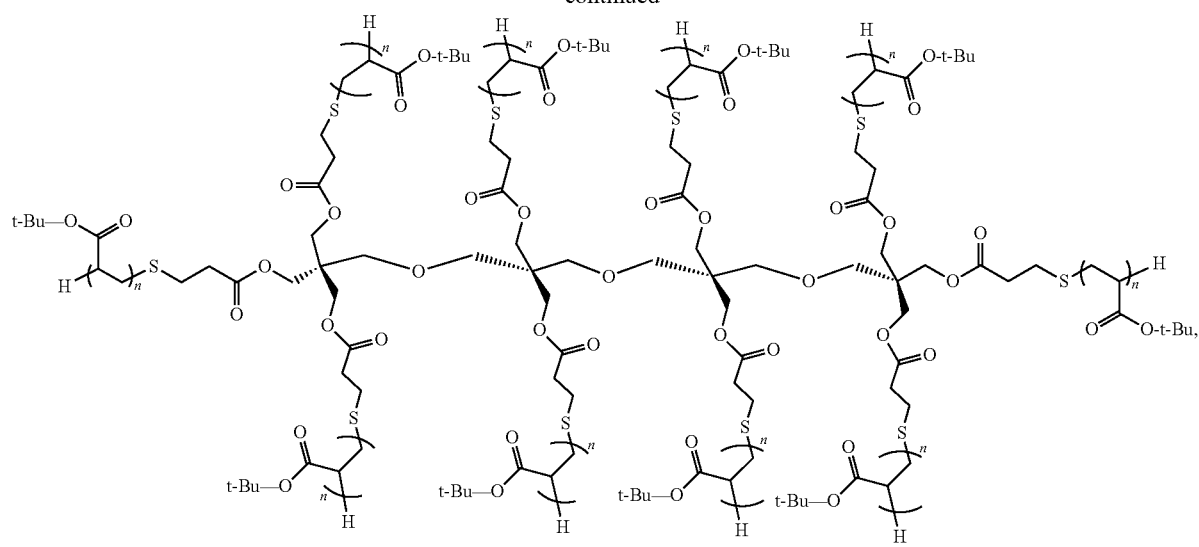
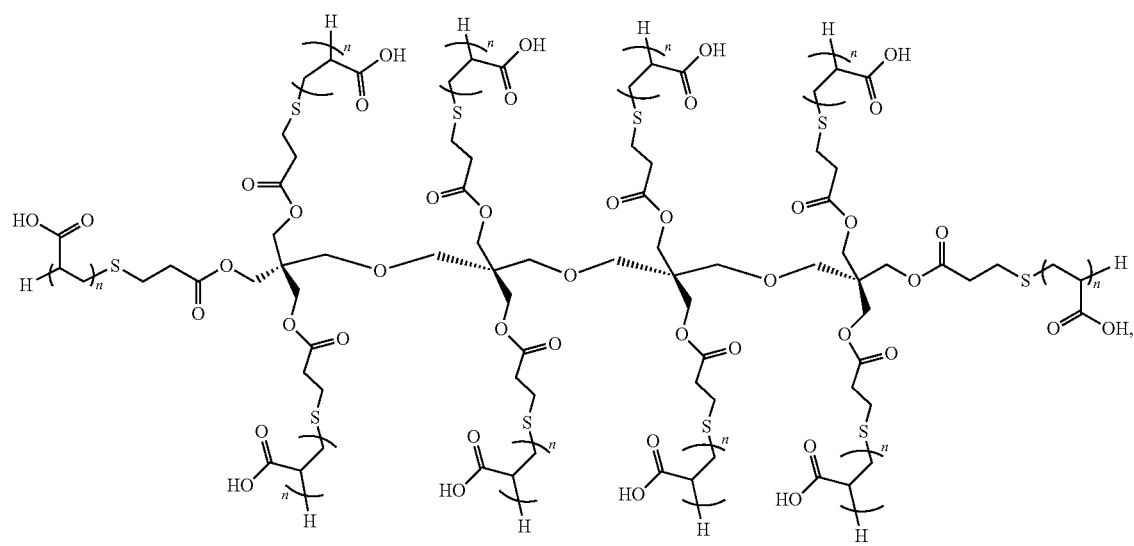
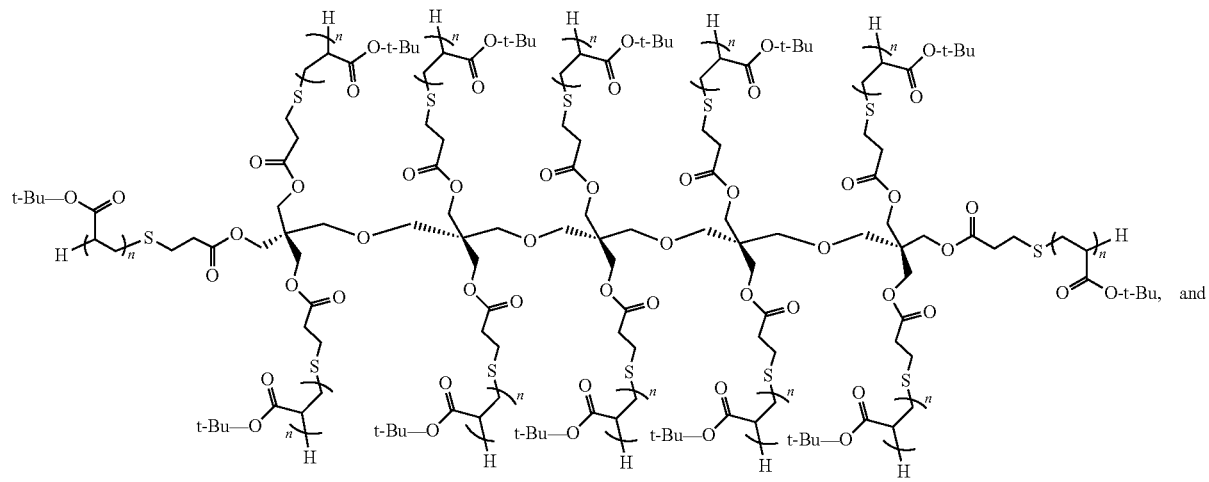

-continued
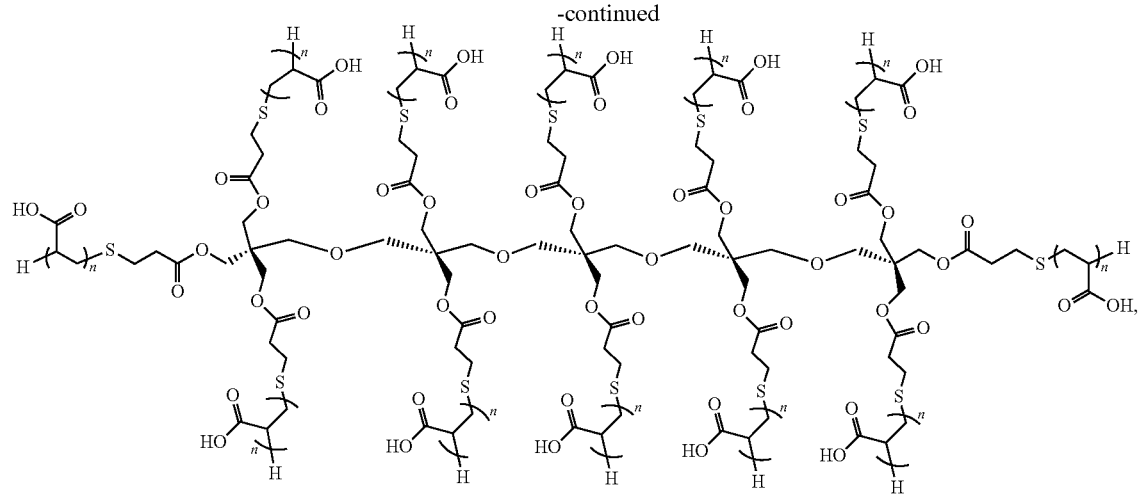
wherein each n and each m are independently in a range of 5 to 500.
* * * * *